United States Patent
Chen et al.

(10) Patent No.: US 10,668,088 B2
(45) Date of Patent: *Jun. 2, 2020

(54) COMBINATION OF 25-HYDROXYVITAMIN D AND ANTIOXIDANTS/ANTI-INFLAMMATORIES FOR HUMAN NUTRACEUTICALS

(71) Applicant: DSM IP ASSETS B.V., Heerlen (NL)

(72) Inventors: Shuen Ei Chen, Kaiseraugst (CH);
Thau Kiong Chung, Kaiseraugst (CH);
Daniel Raederstorff, Kaiseraugst (CH);
Wolfgang Schalch, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/541,793

(22) PCT Filed: Jan. 15, 2016

(86) PCT No.: PCT/EP2016/050762
§ 371 (c)(1),
(2) Date: Jul. 6, 2017

(87) PCT Pub. No.: WO2016/113387
PCT Pub. Date: Jul. 21, 2016

(65) Prior Publication Data
US 2019/0015429 A1     Jan. 17, 2019

Related U.S. Application Data

(60) Provisional application No. 62/103,769, filed on Jan. 15, 2015.

(30) Foreign Application Priority Data

May 8, 2015 (EP) .................................... 15166937
Jun. 18, 2015 (EP) .................................... 15172721

(51) Int. Cl.
| | | |
|---|---|---|
| *A61K 31/593* | (2006.01) | |
| *A23K 20/174* | (2016.01) | |
| *A23L 33/155* | (2016.01) | |
| *A61K 31/047* | (2006.01) | |
| *A61K 31/122* | (2006.01) | |
| *A61K 31/355* | (2006.01) | |
| *A61K 31/375* | (2006.01) | |
| *A61K 31/4188* | (2006.01) | |
| *A61K 31/455* | (2006.01) | |
| *A61K 31/519* | (2006.01) | |

(Continued)

(52) U.S. Cl.
CPC .......... *A61K 31/593* (2013.01); *A23D 7/0053* (2013.01); *A23K 20/158* (2016.05); *A23K 20/174* (2016.05); *A23K 20/179* (2016.05); *A23K 20/30* (2016.05); *A23K 50/75* (2016.05); *A23L 33/105* (2016.08); *A23L 33/15* (2016.08); *A23L 33/155* (2016.08); *A23L 33/16* (2016.08); *A61K 31/01* (2013.01); *A61K 31/015* (2013.01); *A61K 31/045* (2013.01); *A61K 31/047* (2013.01); *A61K 31/05* (2013.01); *A61K 31/065* (2013.01); *A61K 31/122* (2013.01); *A61K 31/197* (2013.01); *A61K 31/355* (2013.01); *A61K 31/375* (2013.01); *A61K 31/4188* (2013.01); *A61K 31/455* (2013.01); *A61K 31/519* (2013.01); *A61K 31/525* (2013.01); *A61K 31/592* (2013.01); *A61K 31/675* (2013.01); *A61K 33/04* (2013.01); *A61K 33/30* (2013.01); *A61K 33/32* (2013.01); *A61K 33/34* (2013.01); *A61K 45/06* (2013.01); *A61P 3/04* (2018.01); *A61P 3/06* (2018.01); *A61P 3/10* (2018.01); *A61P 9/00* (2018.01); *A61P 15/08* (2018.01); *A23V 2002/00* (2013.01)

(58) Field of Classification Search
CPC . A23V 2250/211; A23K 50/75; A23L 33/155; A61P 15/08
See application file for complete search history.

(56) References Cited

U.S. PATENT DOCUMENTS

| | | |
|---|---|---|
| 6,034,075 A | 3/2000 | Thys-Jacobs |
| 7,632,518 B2 | 12/2009 | Tritsch et al. |

(Continued)

FOREIGN PATENT DOCUMENTS

| | | |
|---|---|---|
| CN | 1615139 | 5/2005 |
| CN | 1720030 | 1/2006 |

(Continued)

OTHER PUBLICATIONS

DSM Vitamin Supplementation Guidelines 2011 (https://www.dsm.com/content/dam/dsm/anh/en_US/documents/OVN_supplementation_guidelines.pdf), pp. 1-14 (Year: 2011).*

(Continued)

*Primary Examiner* — Andrew S Rosenthal
(74) *Attorney, Agent, or Firm* — Nixon & Varaderhye P.C.

(57) ABSTRACT

This invention relates to the use of the combination of 25-hydroxyvitamin D3 ("25-OH D3") and antioxidants/anti-inflammatories (ascorbic acid, vitamin E and at least one carotenoid) to make a pharmaceutical, nutraceutical or food supplement which can ameliorate various problems observed in humans connected with polycystic ovarian 5 syndrome and cardiovascular diseases. Pharmaceuticals, nutraceuticals and food supplements containing the 25-OH D3 and antioxidants/anti-inflammatories and premixes are also provided.

1 Claim, 33 Drawing Sheets

(51) Int. Cl.

| | | |
|---|---|---|
| A61K 33/04 | (2006.01) | |
| A61K 33/30 | (2006.01) | |
| A61K 33/32 | (2006.01) | |
| A61K 33/34 | (2006.01) | |
| A23K 50/75 | (2016.01) | |
| A23D 7/005 | (2006.01) | |
| A23K 20/158 | (2016.01) | |
| A61K 31/592 | (2006.01) | |
| A23L 33/15 | (2016.01) | |
| A23L 33/105 | (2016.01) | |
| A61K 31/05 | (2006.01) | |
| A23K 20/20 | (2016.01) | |
| A23L 33/16 | (2016.01) | |
| A61K 31/065 | (2006.01) | |
| A61K 31/045 | (2006.01) | |
| A61K 45/06 | (2006.01) | |
| A23K 20/179 | (2016.01) | |
| A61P 9/00 | (2006.01) | |
| A61P 3/04 | (2006.01) | |
| A61P 3/06 | (2006.01) | |
| A61P 3/10 | (2006.01) | |
| A61P 15/08 | (2006.01) | |
| A61K 31/01 | (2006.01) | |
| A61K 31/015 | (2006.01) | |
| A61K 31/197 | (2006.01) | |
| A61K 31/525 | (2006.01) | |
| A61K 31/675 | (2006.01) | |

(56) References Cited

U.S. PATENT DOCUMENTS

| | | | |
|---|---|---|---|
| 2003/0125229 | A1 | 7/2003 | Rodriguez |
| 2006/0034912 | A1 | 2/2006 | Giordano et al. |
| 2006/0069151 | A1* | 3/2006 | Barella .................. A61K 31/01 514/456 |
| 2010/0098779 | A1 | 4/2010 | Balzer et al. |
| 2010/0112162 | A1 | 5/2010 | Tritsch et al. |
| 2013/0011377 | A1 | 1/2013 | Perrin et al. |
| 2013/0281533 | A1 | 10/2013 | Yamka et al. |

FOREIGN PATENT DOCUMENTS

| | | |
|---|---|---|
| CN | 102215700 | 10/2011 |
| JP | H11-35469 | 2/1999 |
| JP | 2005-519894 | 7/2005 |
| JP | 2006-510647 | 3/2006 |
| JP | 2011-511826 | 4/2011 |
| JP | 2011-511827 | 4/2011 |
| JP | 2012-509253 | 4/2012 |
| SU | 1748784 | 7/1992 |
| WO | WO 2008/031602 | 3/2008 |
| WO | WO 2010/057811 | 5/2010 |
| WO | WO 2014/191153 | 12/2014 |
| WO | WO 2014/202433 | 12/2014 |

OTHER PUBLICATIONS

Rosenfield, R.L. et al. "Dysregulation of cytochrome P450c17 a as the cause of polycystic ovarian syndrome" Fertility and Sterility 1990, 53 (5), 785-791 (Year: 1990).*
Franks, S. "Adult polycystic ovary syndrome begins in childhood" Best Pract Res Clin Endocrinol Metab 2002, 16 (2), 263-272 (Year: 2002).*
Franks, S. "Polycystic Ovary Syndrome" NEJM 1995, 333 (13), 853-861 (Year: 1995).*
International Search Report for PCT/EP2016/050762 dated Apr. 29, 2016, 5 pages.
Written Opinion of the ISA for PCT/EP2016/050762 dated Apr. 29, 2016, 7 pages.
[Online] About DSM: "DSM Vitamin Supplementation Guidelines 2011 Heath @Bullet Nutrition @Bullet Materials for domestic animals Guidelines for Optimum Vitamin Nutrition DSM vitamin supplementation guidelines are designed to provide typical industry practices. Optimum Vitamin Nutrition co", Aug. 11, 2014, pp. 2-3.
Amengual et al., "Beta-Carotene Reduces Body Adiposity of Mice via BCMO1", PLoS ONE, vol. 6, No. 6, Jun. 1, 2011, 14 pages.
Bhuvaneswari et al., "Astaxanthin restricts weight gain, promotes insulin sensitivity and curtails fatty liver disease in mice fed an obesity-promoting diet", Process Biochemistry, vol. 45, No. 8, Aug. 1, 2010, pp. 1406-1414.
Buryakov et al., "Feeding of broiler chicks—involves addn. of sodium ascorbate to basic feed mix to increase live wt. gain", WPI / THOMSON, vol. 1993, No. 27, Jul. 23, 1992.
Muscogiuri et al., "Low Levels of 25(OH) D and insulin-resistance: 2 unrelated features or a cause-effect in PCOS?" Clinical Nutrition, vol. 31, No. 4, pp. 476-480.
Ruschkowski et al., Ionic and Endocrine Characteristics of Reproductive Failure in Calcium-Deficient and Vitamin D-Deficient Laying Hens, Poultry Science, vol. 71, Issue 10, pp. 1722-1732.
Stankiewicz et al., "Macro-elements composition of cystic and follicular fluid in the ovaries and their relationship to peripheral blood concentration in sows", Acta Veterinaria-Beograd, 65(2), 2015, pp. 217-225.
Vanga et al., "Role of Vitamin D in Cardiovascular Health", The American Journal of Cardiology, 2010, pp. 788-805.
Villar-Patiño et al., "Effects of Dietary Supplementation with Vitamin C or Vitamin E on Cardiac Lipid Peroxidation and Growth Performance in Broilers at Risk of Developing Ascites Syndrome", American Journal of Veterinary Research, American Veterinary Medicine Association, vol. 63, No. 5, May 1, 2002, pp. 673-676.
Walzem et al., "Obesity-Induced Dysfunctions in Female Reproduction: Lessons from Birds and Mammals", Advances in Nutrition: An International Review Journal, vol. 5, No. 2, Mar. 1, 2014, pp. 199-206.
International Search Report for PCT/EP2016/050749 dated May 23, 2016, 3 pages.
International Search Report for PCT/EP2016/050751 dated Apr. 26, 2016, 3 pages.
International Search Report for PCT/EP2016/050753 dated Apr. 20, 2016, 3 pages.
International Search Report for PCT/EP2016/050755 dated Apr. 21, 2016, 3 pages.
International Search Report for PCT/EP2016/050759 dated Apr. 26, 2016, 4 pages.
International Search Report for PCT/EP2016/050764 dated Apr. 19, 2016, 3 pages.
Office action for U.S. Appl. No. 15/541,852 dated May 30, 2018 (12 pages).
Office action for U.S. Appl. No. 15/542,091 dated Aug. 10, 2018 (17 pages).
Office action for U.S. Appl. No. 15/542,143 dated Aug. 10, 2018 (14 pages).
Office action for U.S. Appl. No. 15/542,187 dated Jul. 25, 2018 (14 pages).
Office action for U.S. Appl. No. 15/542,500 dated Sep. 10, 2018 (16 pages).
Office action for U.S. Appl. No. 15/542,509 dated Sep. 7, 2018 (16 pages).
Official Action, Colombia Appln. No. NC2017/0007058, Aug. 17, 2018 (English Translation).
Written Opinion of the ISA for PCT/EP2016/050749 dated May 23, 2016, 8 pages.
Written Opinion of the ISA for PCT/EP2016/050751 dated Apr. 26, 2016, 6 pages.
Written Opinion of the ISA for PCT/EP2016/050753 dated Apr. 20, 2016, 6 pages.
Written Opinion of the ISA for PCT/EP2016/050755 dated Apr. 21, 2016, 8 pages.
Written Opinion of the ISA for PCT/EP2016/050759 dated Apr. 26, 2016, 8 pages.

(56) References Cited

OTHER PUBLICATIONS

Written opinion of the ISA for PCT/EP2016/050764 dated Apr. 19, 2016, 8 pages.
Office Action issued in U.S. Appl. No. 15/541,852 dated Dec. 27, 2018.
Office Action issued in U.S. Appl. No. 15/542,091 dated May 23, 2019.
Office Action issued in U.S. Appl. No. 15/542,143 dated Mar. 8, 2019.
Office Action issued in U.S. Appl. No. 15/542,187 dated May 13, 2019.
Office Action issued in U.S. Appl. No. 15/542,500 dated May 23, 2019.
Office Action issued in U.S. Appl. No. 15/542,509 dated May 23, 2019.
Merriam-Webster Medical Dictionary, Medical Definition of supraphysiological, https://www.merriam-webster.com/medical/supraphysiological, retrieved on May 19, 2019.
*Nutrient Requirements of Poultry: Ninth Revised Edition*, The National Academies of Sciences Engineering Medicine, 176 pages (1994).
Garcia et al., "Use of Vitamin D3 and Its Metabolites in Broiler Chicken Feed on Performance, Bone Parameters and Meat Quality" *Asian-Aust. J. Anim. Sci*, vol. 26, No. 3: 408-415 (Mar. 2013); http://dx.doi.org/10.5713/ajas.2012.12455.
Office Action issued in JP Appln. No. 2017-534244 dated Jul. 23, 2019 (w/ translation).
Office Action issued in JP Appln. No. P2017-530279 dated Sep. 3, 2019 (translation).
Cheng et al., "The coupling of epidermal growth factor receptor down regulations and cell cycle arrest in growth suppression of ovarian cancer cells by $1\alpha$, 25-dihydroxyvitamin $D_3$" *Modern Oncology*, vol. 18, No. 2: 229-232 (Feb. 2010).
Liu et al., "A short-term supranutritional vitamin E supplementation alleviated respiratory alkalosis but did of reduce oxidative stress in head stressed pigs" *Asian-Ausralas J Anim Sci*, vol. 31, No. 2: 263-269 (Feb. 2018).
Madar et al., "Effect of vitamin $D_3$ supplementation on glycated hemoglobin (HbA1c) fructosamine, serum lipids, and body mass index: a randomized, double-blinded, placebo-controlled trial among healthy immigrants living in Norway" *BMJ Open Diabetes Research & Care*, vol. 2: e000026, pp. 1-8 (2014).
Nielsen et al., "Elimination of Ascorbic Acid After High-Dose Infusion in Prostate Cancer Patients: A Pharmacokinetic Evaluation" *Basic & Clinical Pharmacology & Toxicology*, vol. 116: 343-348 (2015).
Quaranta et al., "The effects of 'supra-physiological' vitamin $B_{12}$ administration on temporary threshold shift" *International Journal of Audiology*, vol. 43: 162-165 (2004).
Vollbracht et al., "Commentary: Supraphysiological vitamin B12 serum concentrations without supplementation: the pitfalls of interpretation" *QJM. An International Journal of Medicine*, vol. 0, No. 0: 1-2 (2019).
Witmer et al., "Direct spectrophotometric measurement of supraphysiological levels of ascorbate in plasma" *Redox Biology*, vol. 8: 298-304 (2016).

\* cited by examiner

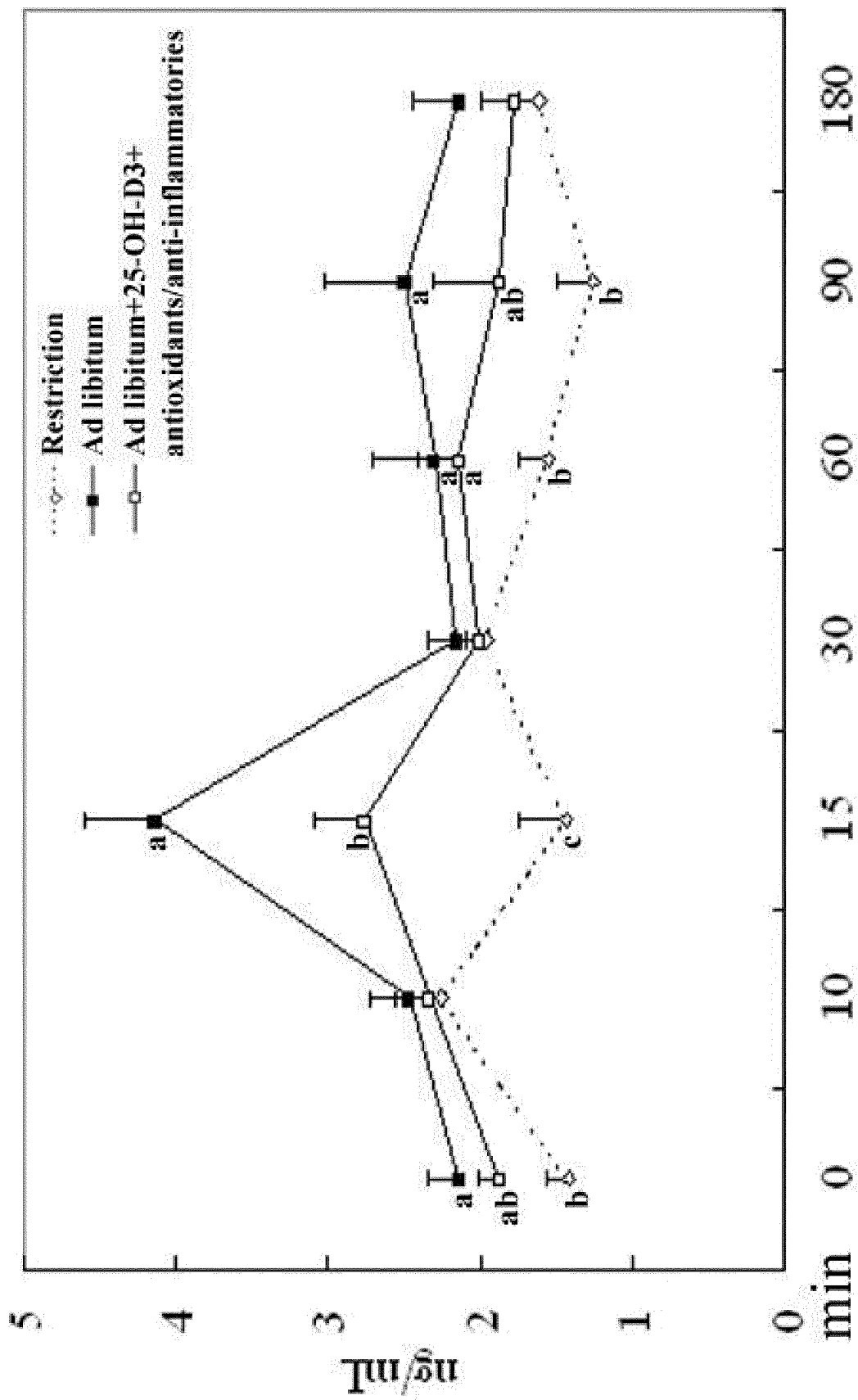
FIGURE 1, ctd.

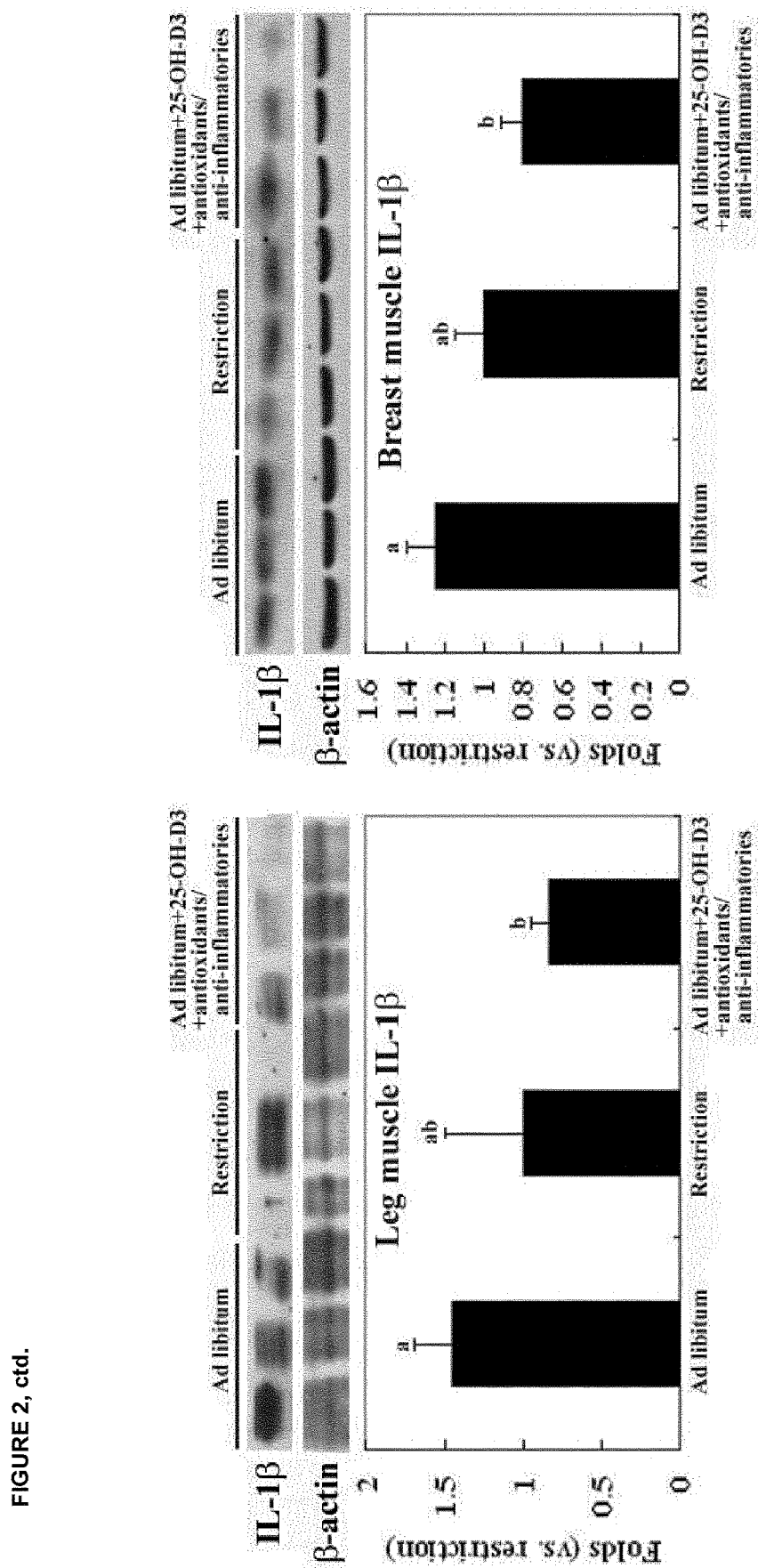
FIGURE 2, ctd.

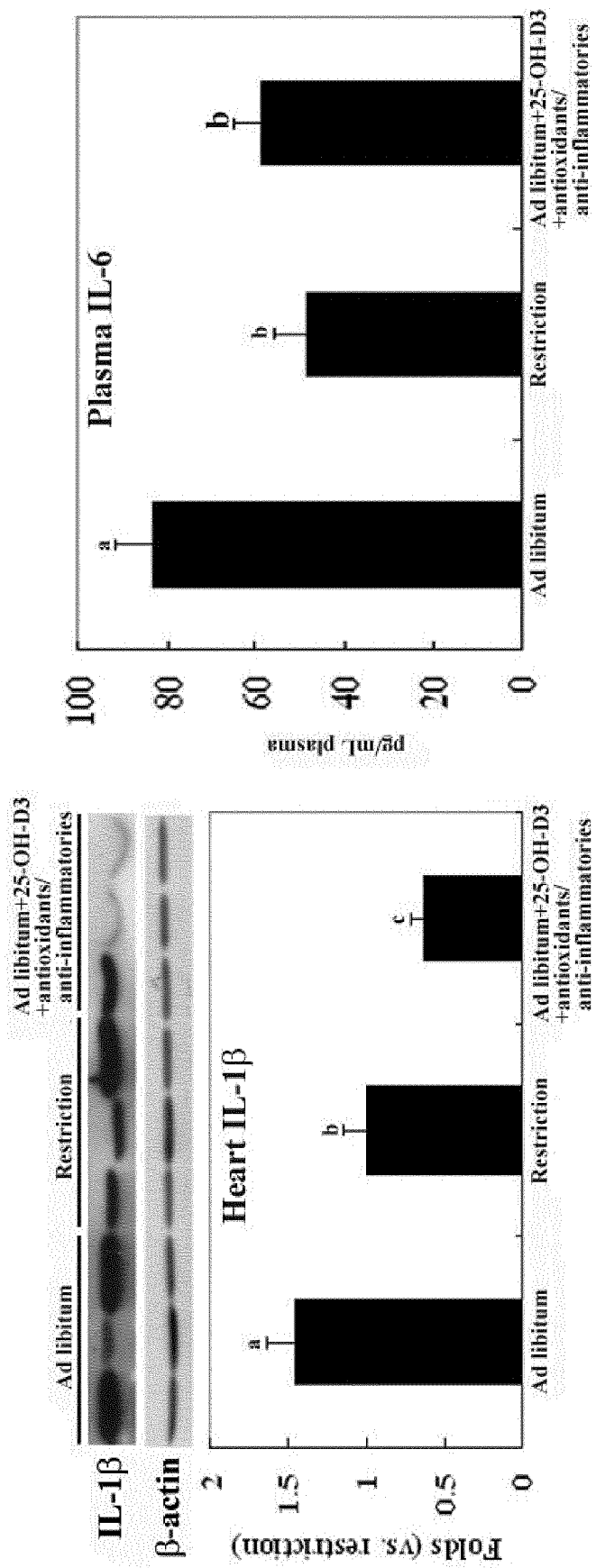
FIGURE 2, ctd.

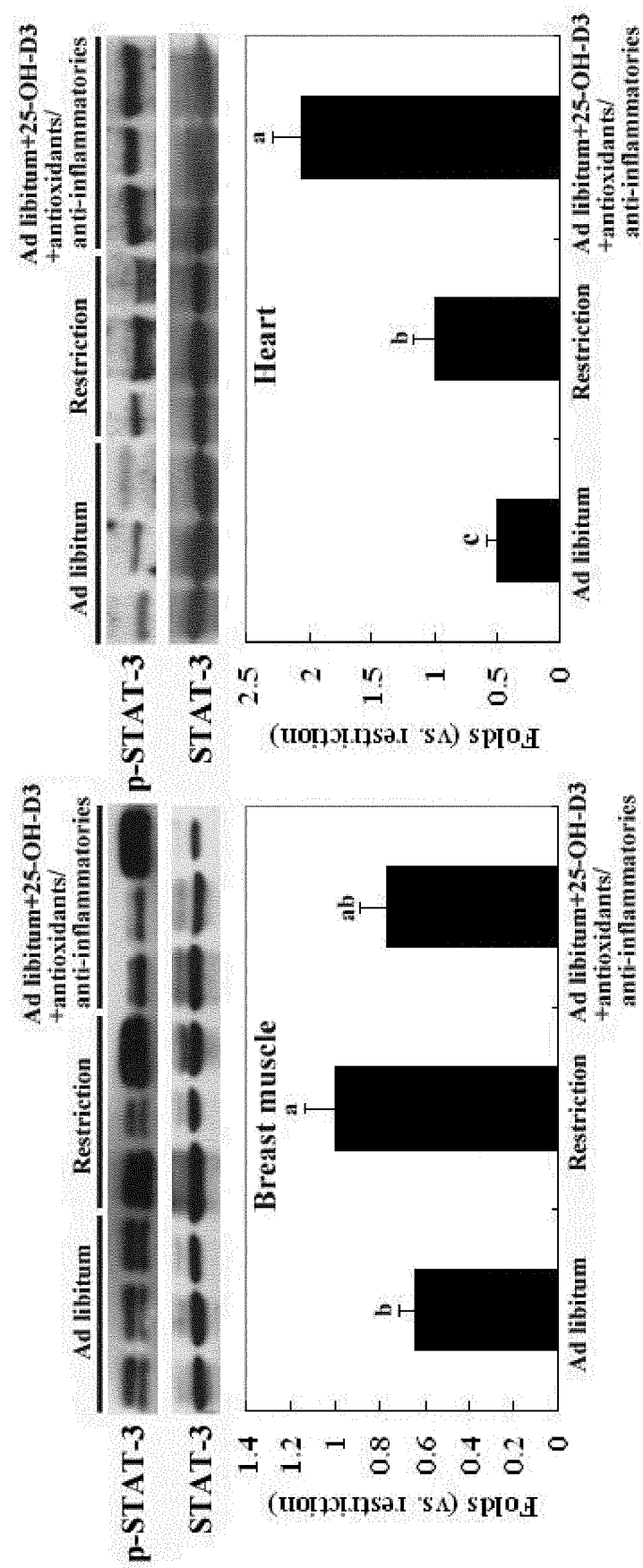
FIGURE 3, ctd.

Effusion in pericardial cavity

FIGURE 10 A  Ascites

FIGURE 10, ctd.

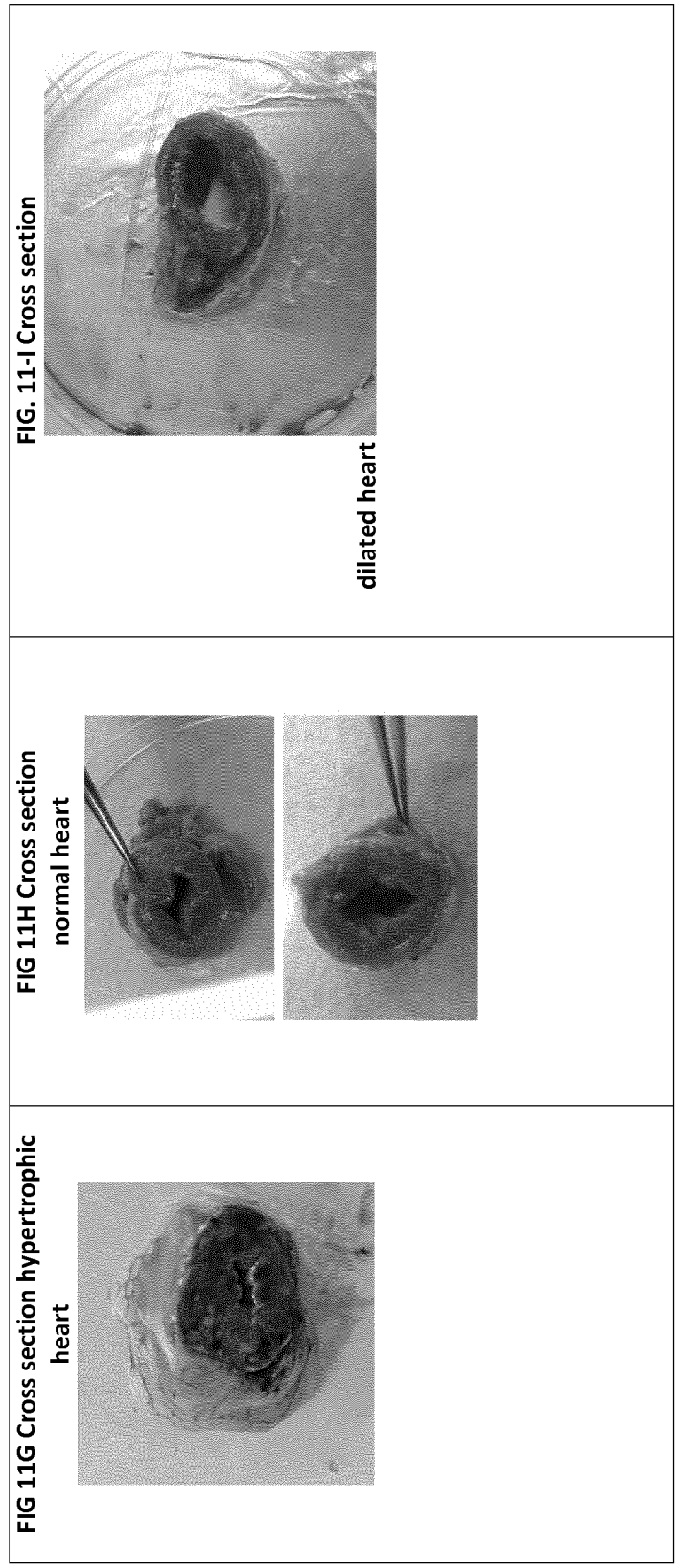
FIGURE 11, Ctd.

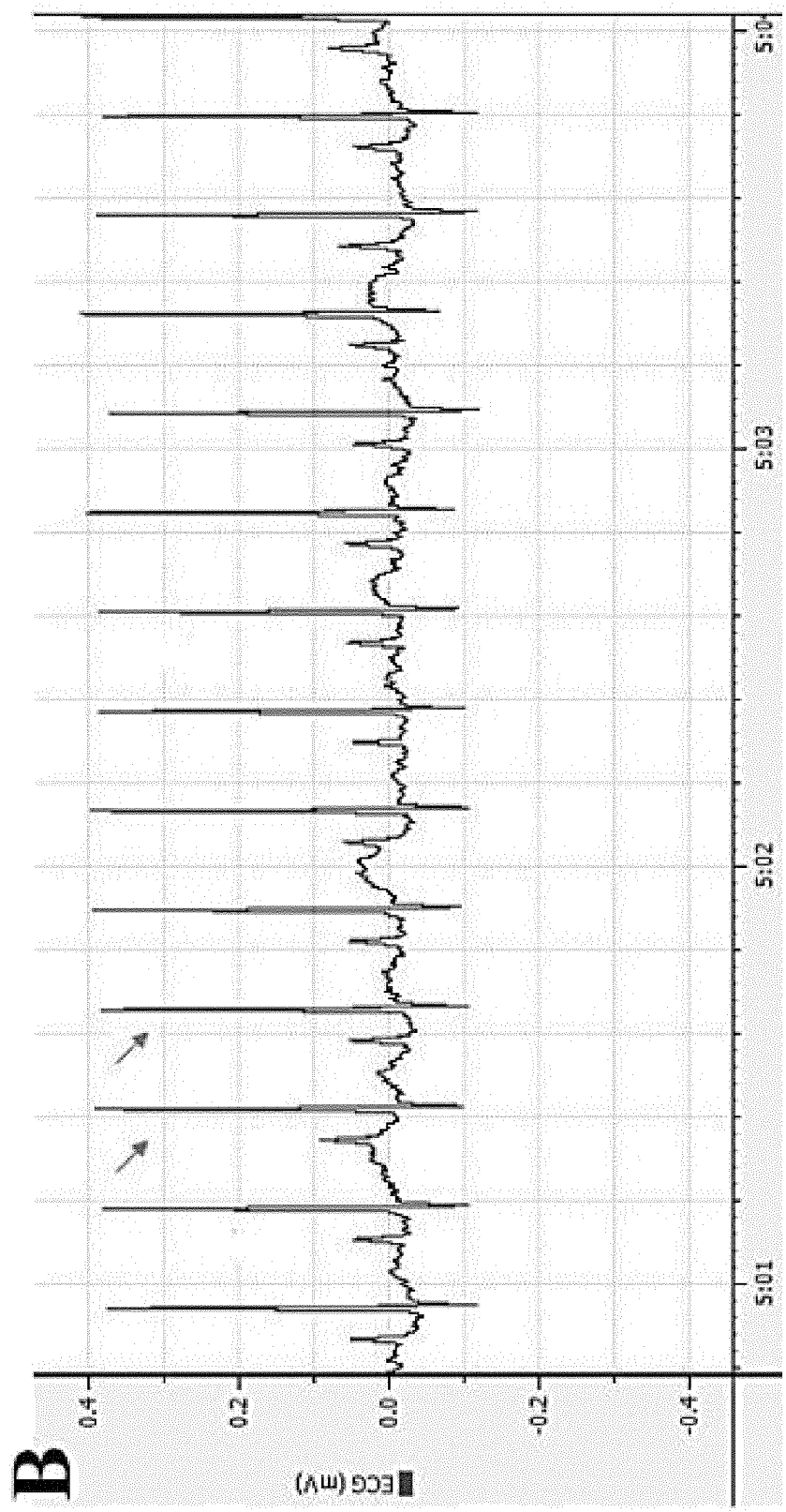
FIGURE 12, Ctd.

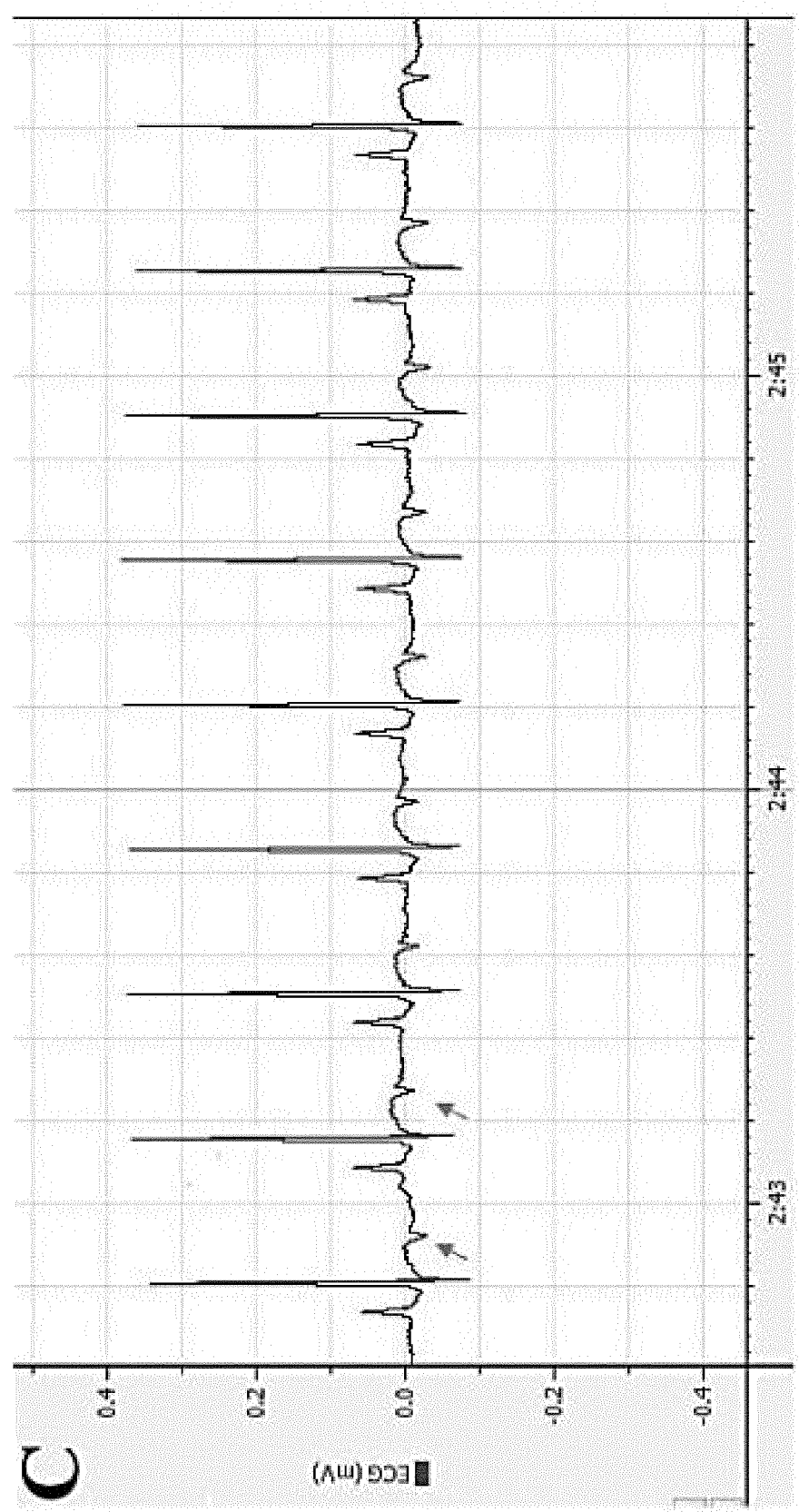
FIGURE 12, Ctd.

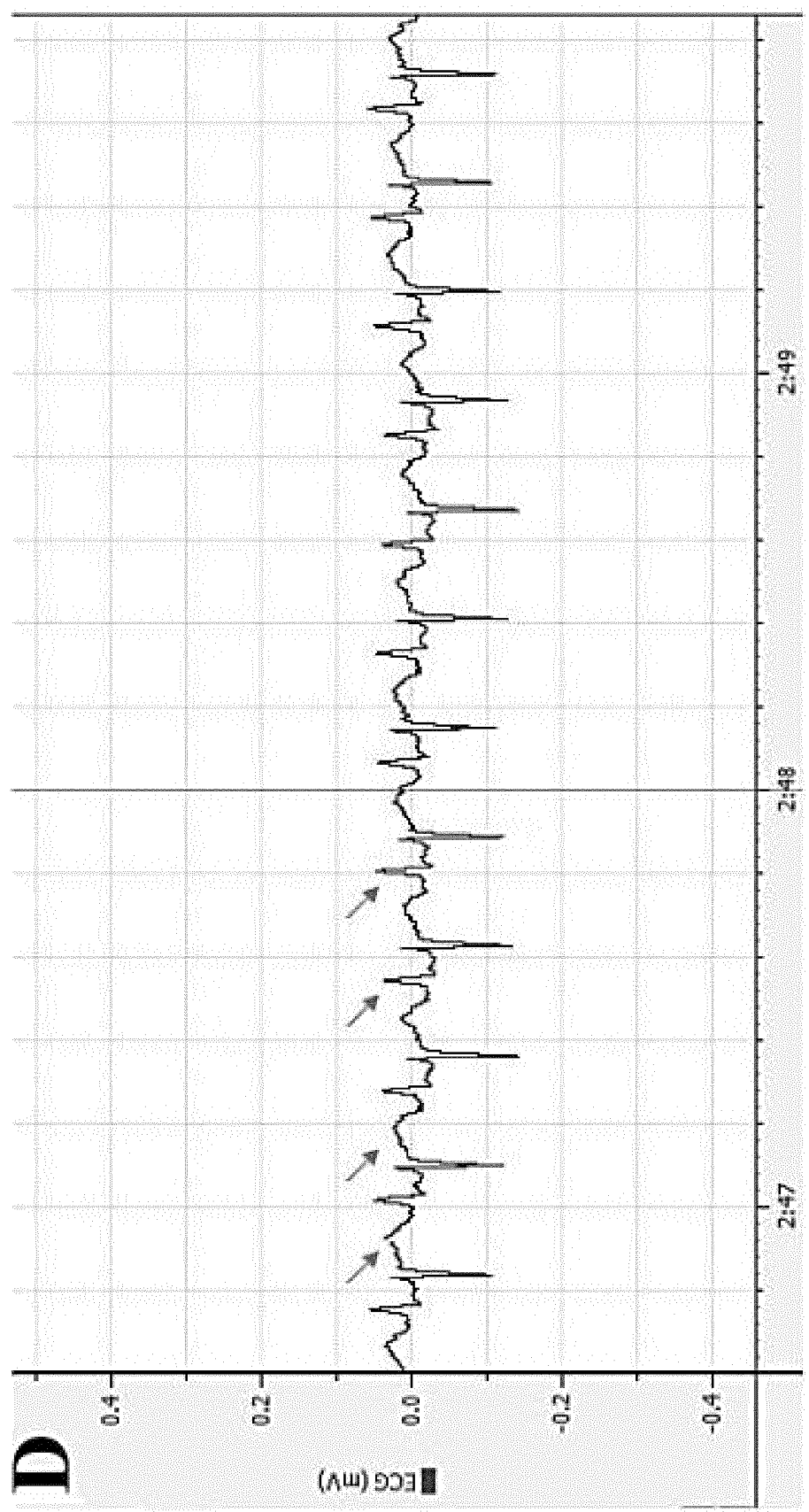
FIGURE 12, ctd.

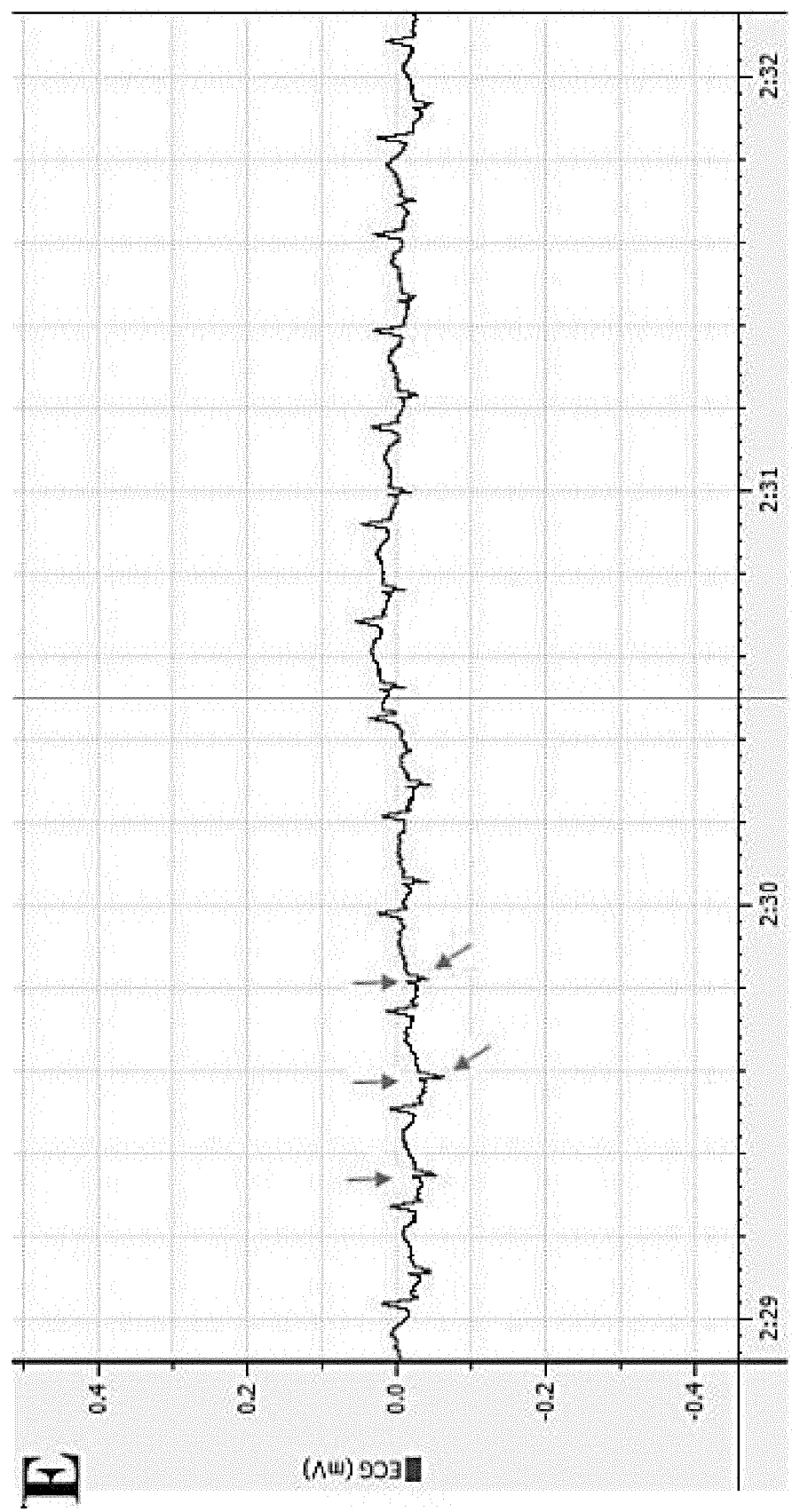
FIGURE 12, CTD.

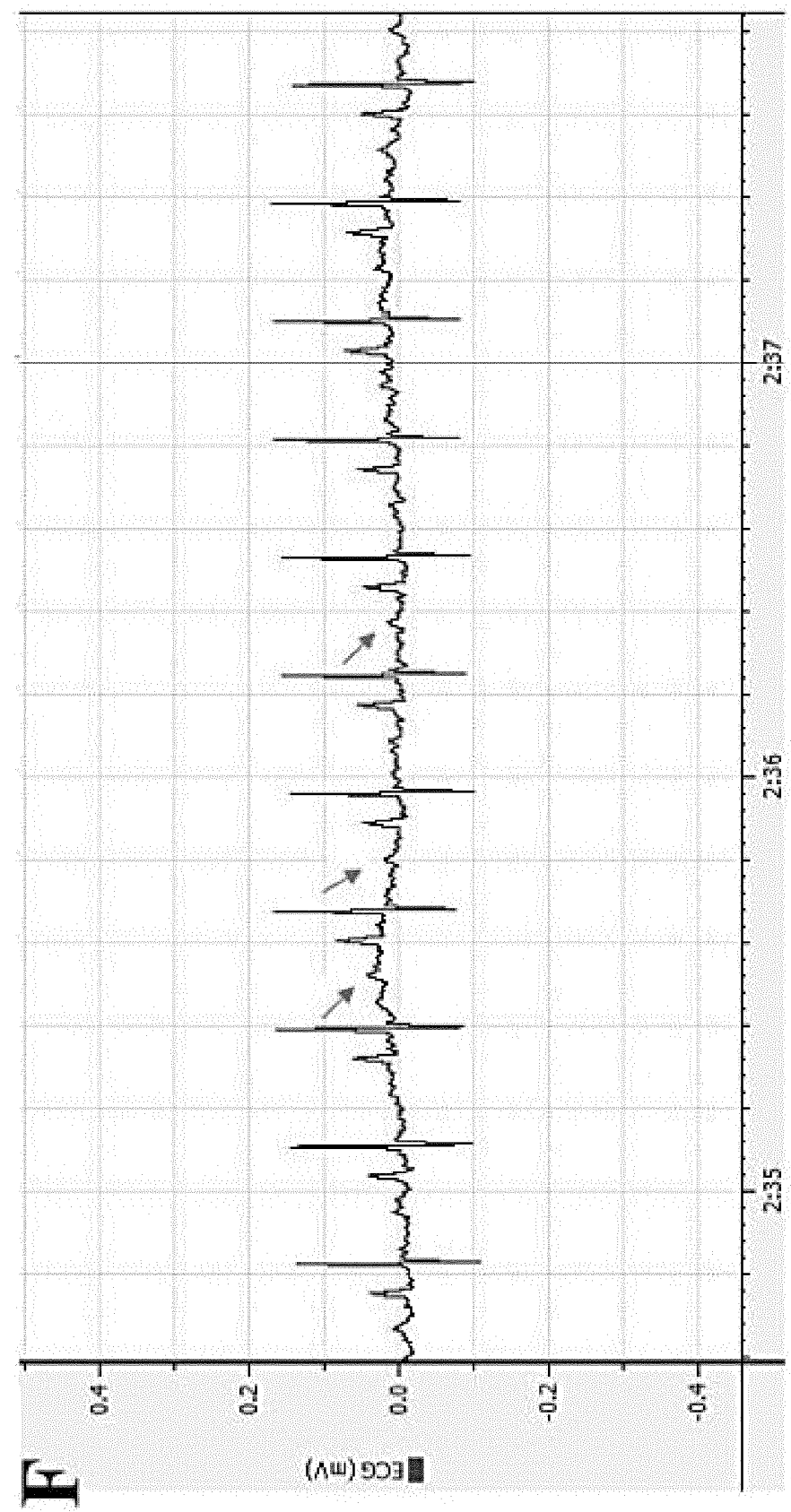
FIGURE 12, CTD.

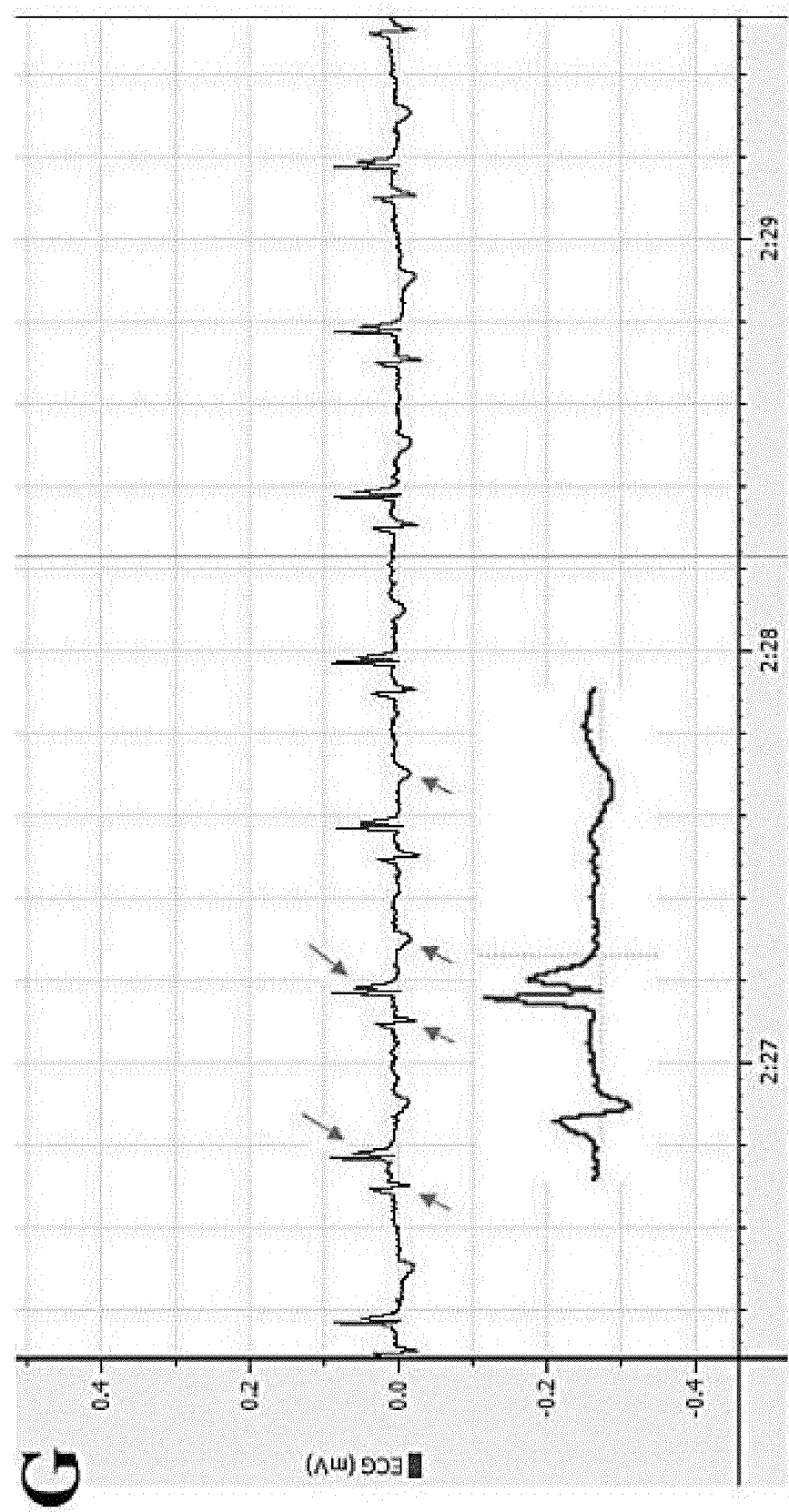
FIGURE 12, ctd.

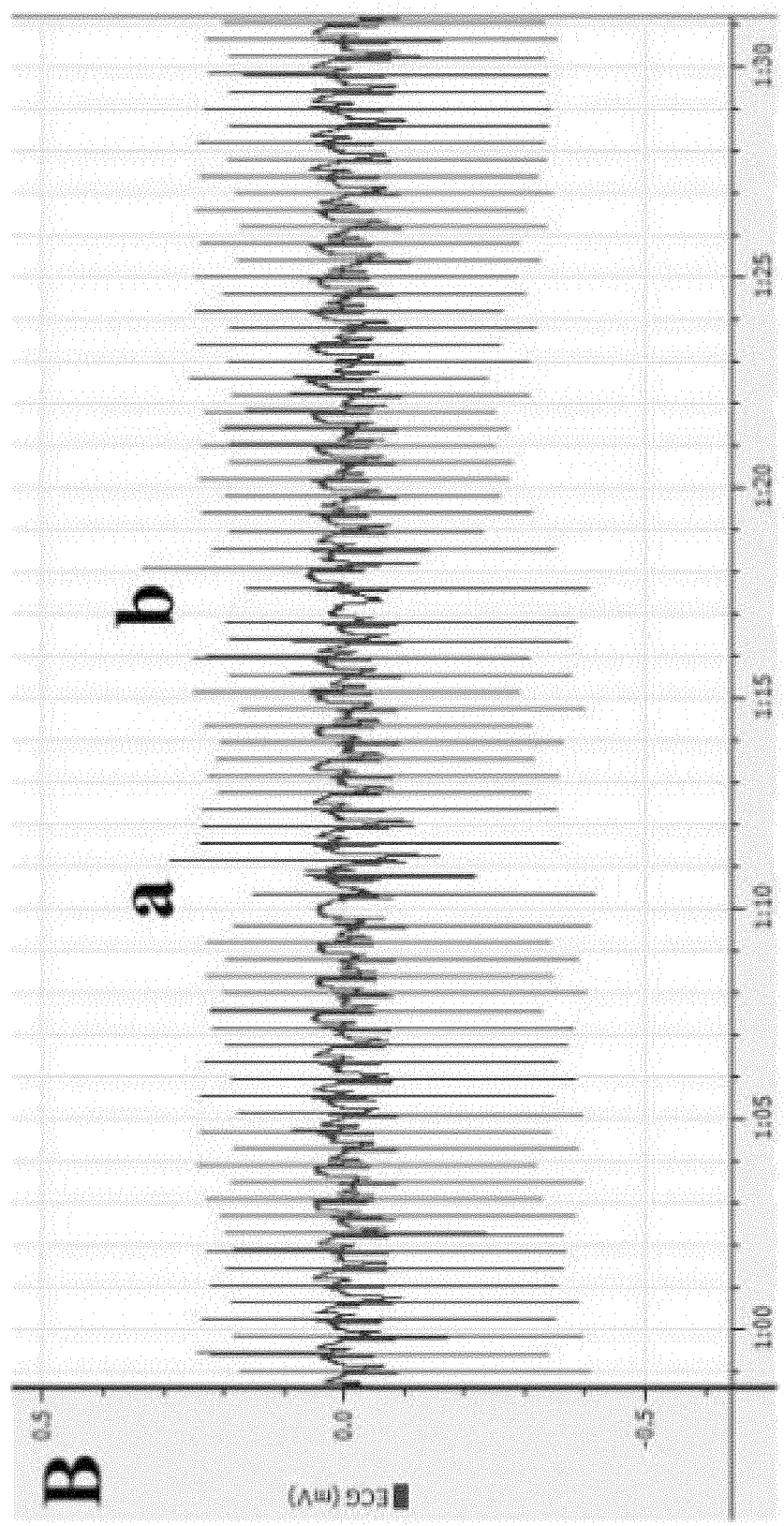
FIGURE 13, ctd.

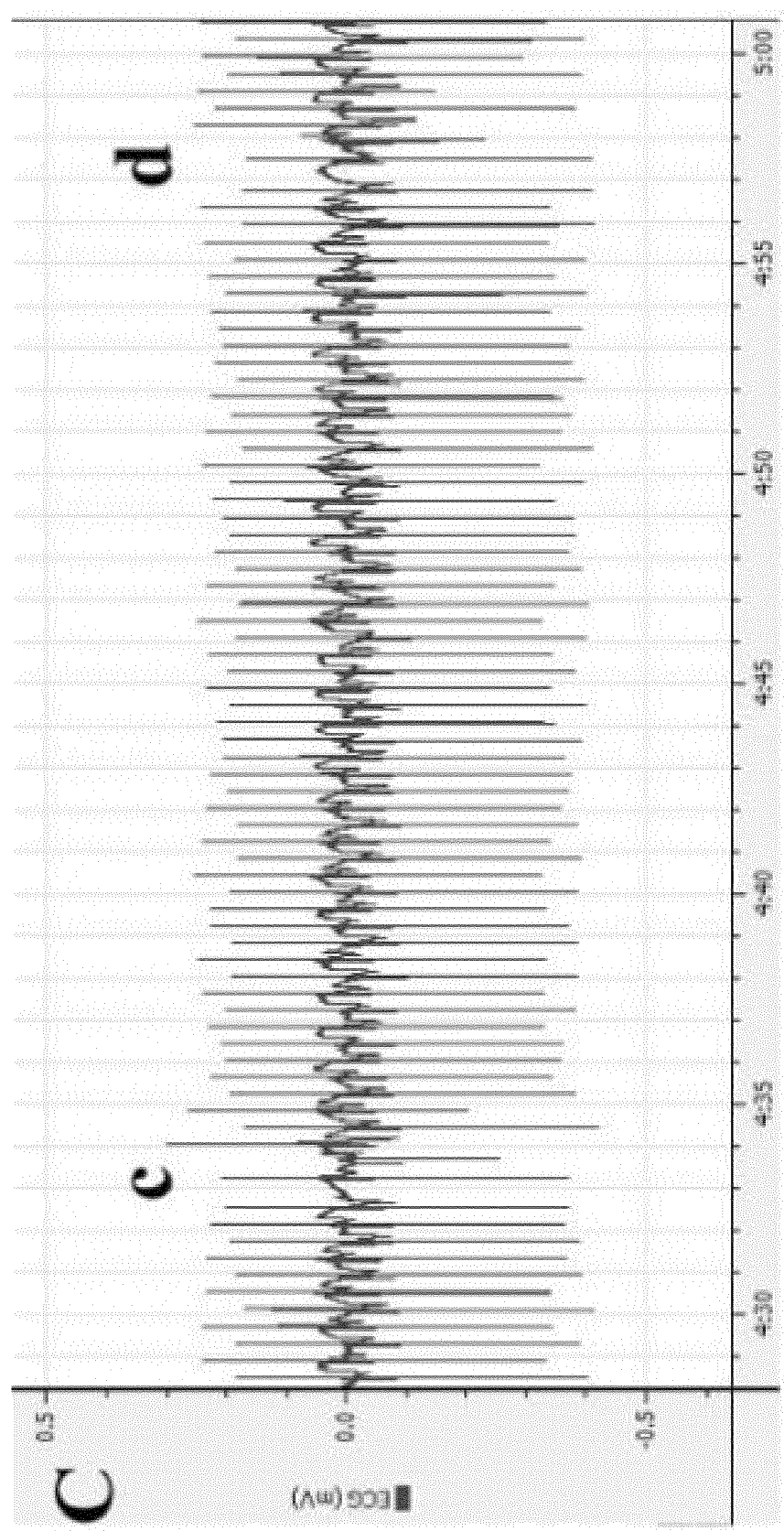
FIGURE 13, ctd.

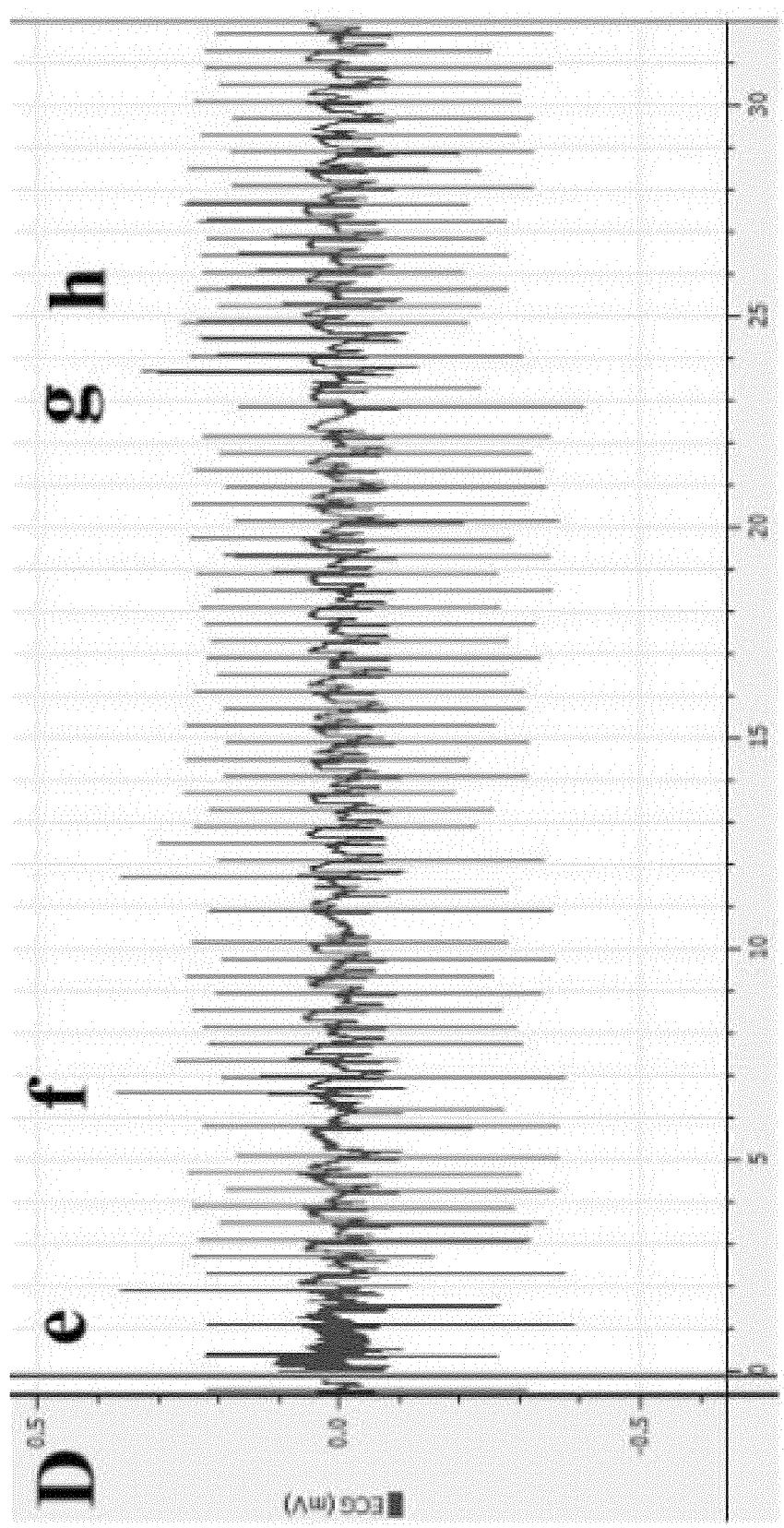
FIGURE 13, ctd.

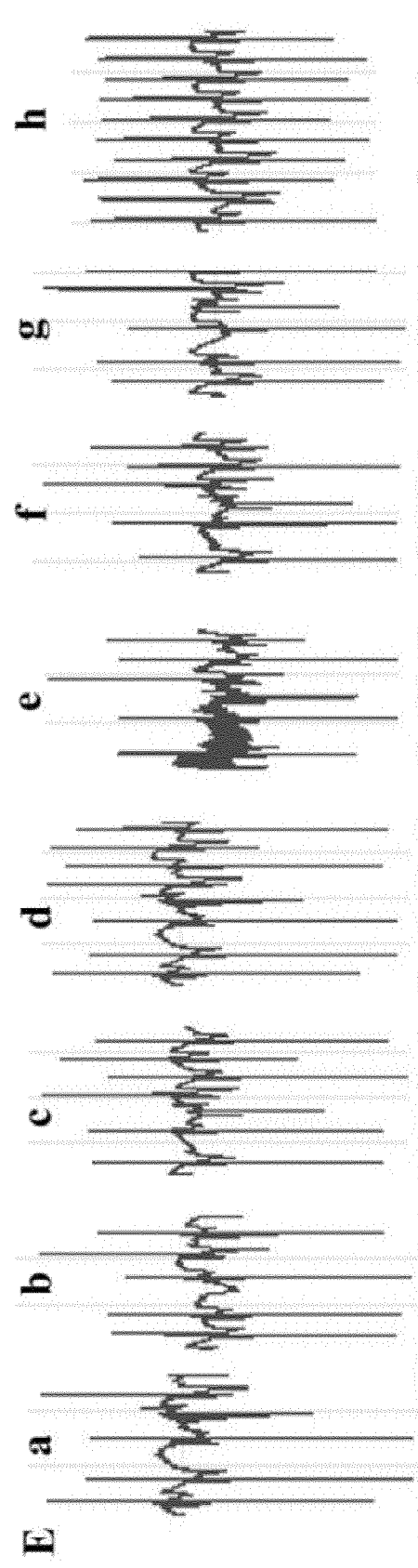
FIGURE 13, ctd.

COMBINATION OF 25-HYDROXYVITAMIN D AND ANTIOXIDANTS/ANTI-INFLAMMATORIES FOR HUMAN NUTRACEUTICALS

This application is the U.S. national phase of International Application No. PCT/EP2016/050762 filed Jan. 15, 2016 which designated the U.S. and claims the benefit of U.S. Provisional Application No. 62/103,769 filed Jan. 15, 2015 and claims priority to EP Patent Application No. 15166937.1 filed May 8, 2015 and EP Patent Application No. 15172721.1 filed Jun. 18, 2015 the entire contents of each of which are hereby incorporated herein by reference.

BRIEF DESCRIPTION OF THE INVENTION

This invention relates to the combination of 25-hydroxyvitamin D ("25-OH D3" and/or "25-OH D2") and antioxidants/anti-inflammatories (ascorbic acid, Vitamin E and a carotenoid) for use in human nutraceuticals, pharmaceuticals and food supplements. This combination of nutritional supplements protects against various adverse effects associated with hyperphagia and related obesity. It also relates to nutraceuticals, nutraceutical premixes, pharmaceuticals and food containing the combination of 25-hydroxyvitamin D and the antioxidants/anti-inflammatories.

BACKGROUND OF THE INVENTION

Hyperphagia (overeating) and its related obesity can cause various problems in humans. These problems include: ovarian dysfunction and infertility as well as metabolic disorders related to the cardiovascular system and the blood sugar system.

Interestingly, one animal model for female ovarian disease is poultry. The domestic laying hen is the only non-human animal that develops ovarian cancer with a high prevalence. See Johnson et al 2013 *Nature* 13: 432-436, and Walzem et al 2014 *Advances in Nutrition* 5: 199-206. The progression of hen ovarian cancer as well as locations of metastatic growths and ascites are similar to that observed in women.

Some breeds of poultry experience hyperphagia-related obesity. Generally, the farmer will restrict the amount of food offered to the flock to prevent the adverse consequences of obesity. However, it is often difficult to determine the proper amount of feed to provide which will ensure the desired growth of the flock, and under restricted feeding conditions, individuals can become aggressive and not only injure other birds, but become obese themselves.

Female broiler breeders overfed during reproductive development not only produce excess large yellow ovarian follicles but also generate a greater number of atretic yellow follicles and commonly display erratic oviposition and defective egg syndrome (EODES) that include several reproductive problems such as follicular atresia, the production of soft-shelled or membranous eggs, double-yolked eggs, egg yolk peritonitis (presence of egg yolk in the abdominal cavity), multiple egg days and oviposition not occurring in sequence, resulting in increased production of unsettable eggs.

Controlled studies reported that voluntary feeding (i.e., broiler breeder hens fed to satiation) resulted in poor egg production, high rate of mortality and abnormal ovarian structure (mainly overt hierarchical follicle atresia). In contrast to feed-restricted hens, voluntary feeding also induced metabolic dysregulations that comprised enhanced adiposity; hepatic triacylglycerol accumulation; and elevated concentrations of plasma glucose, non-esterified fatty acids, very low density lipoprotein, triacylglycerol, phospholipids, ceramide and sphingomyelin.

Furthermore, hepatic and circulating ceramide and sphingomyelin accumulation, and up-regulation of proinflammatory IL-1β expression in liver and adipose tissues systemically manifested the development of lipotoxicity in feed-satiated hens. Ceramide is a key intermediate linking certain nutrients (i.e. saturated fats) and inflammatory cytokines (e.g. tumor necrosis factor-α, TNFα) to the regulation of cell function and antagonizing insulin signaling and mitochondrial function. Moreover, as a result of its toxic effects on particularly susceptible cell types, ceramide has the capacity to damage the heart, pancreas, and vasculature. Lipotoxicity leading to impaired ovarian dysfunctions, including follicle atresia, ovarian regression, and a decline of circulating estradiol levels in feed-satiated hens, was further exemplified by ceramide accumulation and up-regulation of IL-1β, serine palmitoyltransferase, and sphingomyelinase transcript abundance, but suppressed protein kinase Akt activation within the hierarchical follicles. In vivo evidence has thus delineated the actions of ceramide and IL-1β in mediating overfeeding-induced follicle atresia and progression of ovarian involution in broiler hens.

Despite restricted feeding regimen strictly implemented in commercial broiler breeder flocks, it is still very easy to overfeed breeder hens due to their intrinsic hyperphagia. Furthermore, breeder farm managers are confronted as to when and how to feed before and during the start of egg production as well as towards, during and after peak production. The basic fundamental question to ask what and how management and nutritional tools breeder farm managers can apply and implement to ameliorate the adverse and deleterious effects of reproductive efficiency associated with obesity in overweight hens.

Hy·D® (registered trademark for 25-OH-D3; available from DSM Nutritional Products, Switzerland) has been used to promote bone health in poultry, swine, and for vitamin D deficiency in humans.

The combination of 25-OH D3 and canthaxanthin has also been used in poultry. WO2010/057811 (DSM IP ASSETS, BV) describes this combination for use in improving hatchability, fertility, and lower embryo mortality in poultry. The combination is commercially available under the trademark MAXICHICK. There is no mention in the patent publication of the inclusion of ascorbic acid and high vitamin E levels, nor the uses to ameliorate the adverse effects of hyperphagia-related obesity.

Vitamin C (ascorbic acid) is often not included as a supplement in poultry diets, as the chicken can under normal rearing conditions can produce sufficient Vitamin C. However, it has been used in some specific conditions, such as in heat stress situations.

Vitamin E is generally added to poultry feed. Recommended doses for poultry species tends to range from about 50-100 IU/kg feed, depending on the age of the animal.

WO14/202433 (DSM IP ASSETS B.V) teaches the combination of canthaxanthin and 25-OH D3 to improve internal egg quality, i.e. enhancing the strength of vitelline membrane that envelops the yolk. There is no teaching to add ascorbic acid to the combination, nor for its use in ameliorating the adverse effects of hyperphagia-related obesity.

WO14/191153 (DSM IP ASSETS B.V) teaches the combination of canthaxanthin and at least one of Vitamin C, Vitamin E, selenium, and optionally at least one of thymol, eugenol, vanillin and gamma-terpinene can improve immune statues, bone health, skeletal development and growth and feed conversion, particularly when flocks are subject to stress associated with vaccination.

There is a need to prevent or delay the onset of ovarian diseases and cardiovascular related problems in humans, as well as to modulate weight gain associated with hyperphagia.

DETAILED DESCRIPTION OF THE INVENTION

It has been found, accordance with this invention that the combination of 25-hydroxyvitamin D (25-OH D3 and/or 25-OH D2) and antioxidants/anti-inflammatories can benefit ovarian health, and particularly polycystic ovarian syndrome. In addition to benefiting ovarian health, the combination of 25-OH D and antioxidants/anti-inflammatories can benefit cardiovascular and metabolic health and modulate weight gain in people who overeat. It has also been found in accordance with this invention, that the bio-actives traditionally thought of as antioxidants also possess an anti-inflammatory activity which benefits ovarian and cardiovascular health.

As 25-OH D2 and 25-OH D3 may act in a similar fashion after administration, it is envisioned that either may be used separately in combination with antioxidants/anti-inflammatories, or a mixture of both 25-OH D3 and 25-OH D2 may be used in combination with antioxidants/anti-inflammatories. If used together, the ratio of 25-OH D3: 25-OH D2 is not a critical part of the invention. 25-OH D3 used alone is preferred.

The antioxidants/anti-inflammatories of this invention comprise the combination of ascorbic acid, vitamin E and a carotenoid. The carotenoid is at least one selected from the group consisting of: lycopene, astaxanthin, cryptoxanthin, beta-carotene, lutein, zeaxanthin and canthaxanthin. Most preferred are lycopene, astaxanthin, lutein, and zeaxanthin. Thus one aspect of this invention is the combination of 25-OH D3, one or more of the aforementioned carotenoids, vitamin E and ascorbic acid. Another embodiment is the combination of 25-OHD2, one or more of the aforementioned carotenoids, Vitamin E and ascorbic acid. Another embodiment is the combination of 25-OHD3, 25-OHD2, one or more of the aforementioned, Vitamin E and ascorbic acid.

Compositions

Another aspect of this invention is the combination of 25-OH D, one or more of the aforementioned carotenoids, Vitamin E and ascorbic acid, which optionally further comprises at least one further bio-active ingredient selected from the group consisting of:

Vitamin D, Vitamin B2, Biotin, Vitamin B6, Niacin, Zinc, Copper, Manganese, and Selenium. Preferably the 25-OH D is 25-OH D3. Preferably at least Vitamin D is a further bio-active ingredient. Sometimes the further bio-active ingredients include at least Vitamin D and Selenium. In some cases, all the further bio-active ingredients are added.

A further aspect is the combination of 25-OH D, one or more carotenoids of this invention, vitamin E and ascorbic acid which optionally further comprises at least one further bio-active ingredient selected from the group consisting of Vitamin D, Vitamin B2, Vitamin B6, Niacin, Pantothenic Acid, Folic Acid, Biotin, Zinc, Copper, Manganese, Selenium, and combinations thereof. Preferably the 25-OH D is 25-OH D3. Sometimes, the further bio-active ingredient includes biotin. Sometimes the further bio-active ingredient includes Vitamin D and biotin. Sometimes the further bio-active ingredient includes all the aforementioned optionally bio-active ingredients.

Nutraceuticals, Pharmaceuticals, Dietary Supplements

Another aspect of this invention is a nutraceutical such as a dietary supplement, or pharmaceutical comprising the combination of 25-OH D2 or 25-OH D3 or mixtures thereof, ascorbic acid, Vitamin E and one or more of the aforementioned carotenoids.

Yet another embodiment is a nutraceutical such as a dietary supplement, or a pharmaceutical comprising the combination of 25-OH D, one or more of the aforementioned carotenoids, vitamin E and ascorbic acid, which optionally further comprises at least one further bio-active ingredient selected from the group consisting of: Vitamin D, Vitamin B2, Vitamin B6, Niacin, Zinc, Copper, Manganese, Selenium and combinations thereof. Preferably the 25-OH D is 25-OH D3. Sometimes the further bio-active ingredients include at least Vitamin D and Selenium. In some cases, all the further bio-active ingredients are added.

Another embodiment is a nutraceutical, such as a dietary supplement or a pharmaceutical comprising the combination of 25-OH D, one or more of the aforementioned carotenoids, vitamin E and ascorbic acid, which optionally further comprises at least one further bio-active ingredient selected from the group consisting of: Vitamin D, Vitamin B2, Vitamin B6, Niacin, Pantothenic Acid, Folic Acid, Biotin, Zinc, Copper, Manganese, Selenium and combinations thereof. Sometimes, the further bio-active ingredient includes biotin. Preferably the 25-OH D is 25-OH D3. Sometimes the further bio-active ingredient includes Vitamin D and biotin. Sometimes the further bio-active ingredient includes all the aforementioned optionally bio-active ingredients.

Premixes

Another aspect of this invention are premixes for nutraceuticals, such as food supplements or vitamin supplements which comprise the combination of 25-OH D, vitamin E, ascorbic acid and one or more of the aforementioned carotenoids. Preferably, the 25-OH D is 25-OH D3. The premixes and subsequent nutraceutical improves/ameliorates adverse conditions associated with the ovaries, and specifically polycystic ovarian syndrome. In some embodiments the premix or subsequent nutraceutical also comprises at least one further bio-active ingredient selected from the group consisting of:

Vitamin D, Vitamin B2, Vitamin B6, Niacin, Zinc, Copper, Manganese, Selenium and combinations thereof. Sometimes the further bio-active ingredients include at least Vitamin D and Selenium. In some cases, all the further bio-active ingredients are added.

Another aspect of this invention are premixes for nutraceuticals which comprise which further comprise at least one further bio-active ingredient selected from the group consisting of: Vitamin D, Vitamin B2, Vitamin B6, Niacin, Pantothenic Acid, Folic Acid, Biotin, Zinc, Copper, Manganese, Selenium and combinations thereof. Sometimes, the further bio-active ingredient includes biotin. Sometimes the further bio-active ingredient includes Vitamin D and biotin. Sometimes the further bio-active ingredient includes all the aforementioned optionally bio-active ingredients.

When using the nutraceuticals or pharmaceuticals of this invention, the person may eat normally or over-eat, and the ill effects which affect the ovaries, cardiovascular system and metabolic system and are normally associated with eating a non-calorie restricted diet will be experienced to a lesser degree or not at all.

Figure 1:
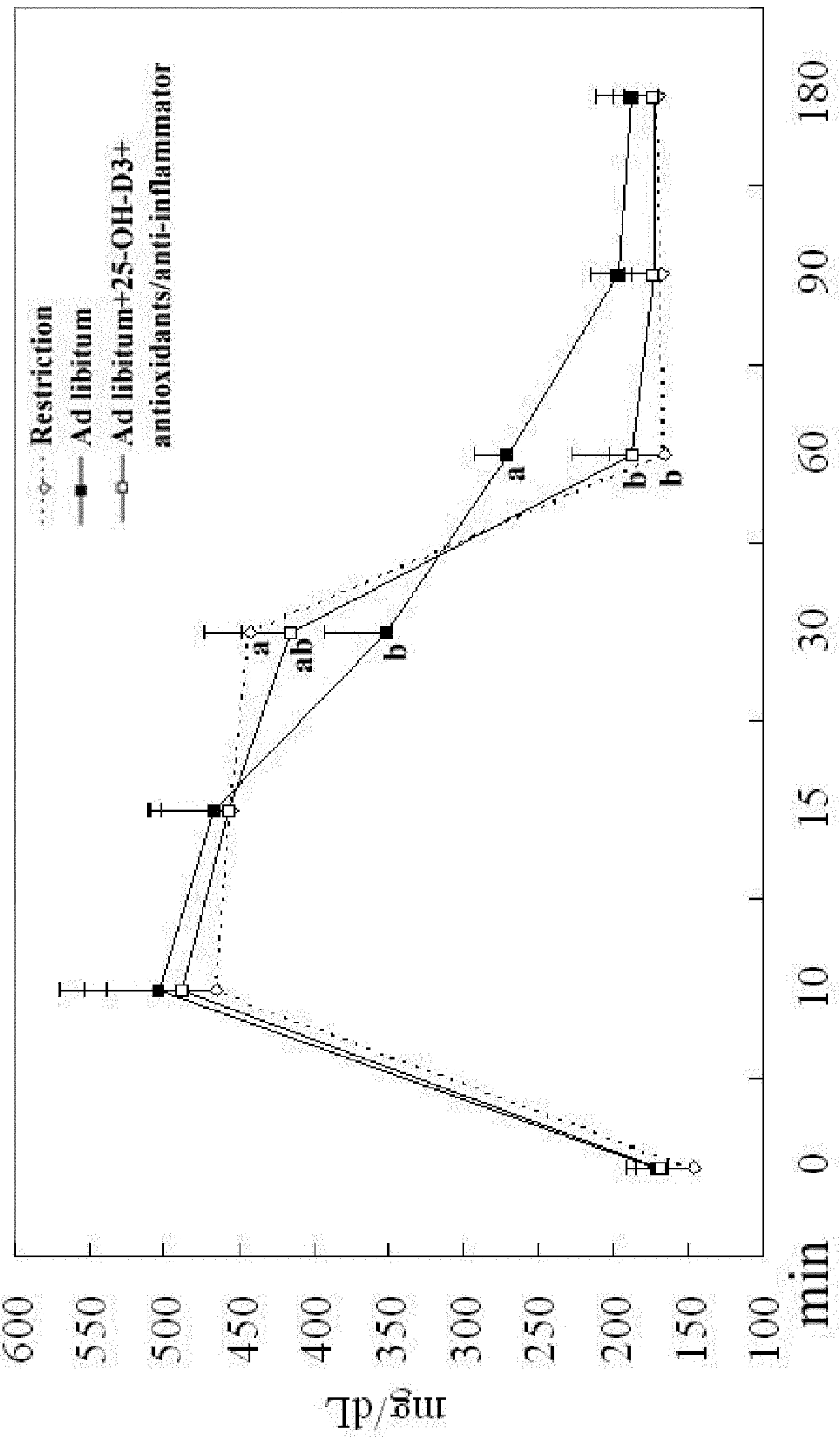
FIG. 1 shows glucose clearance and insulin secretion of broiler breeder hens in response to ad libitum feed intake in combination with 25-OH D3+antioxidants/anti-inflammatories. Hens were injected with a single dose of glucose (0.5 g/kg BW) through wing vein after 3 weeks of feeding. Blood samples were collected through cannulation of wing vein at indicated time points after glucose infusion, n=3.

As used throughout this specification and claims, the following definitions apply: "25-OH D" refers to any form of 25-hydroxyvitamin D (i.e. either 25-OH D2 or 25-OH D3, or mixes thereof). 25-OH D3 specifically refers to 25-hydroxyvitamin D3; 25-OH D2 specifically refers to 25-hydroxyvitamin D2.

"Vitamin D" means either Vitamin D2, Vitamin D3 or a combination. Vitamin D3 used alone is preferred.

"Hyperphagia" is excessive eating; the person's intake of calories is greater than their energy expenditure.

"Ameliorating weight gain" means that there is a significantly lower amount of weight gain when eating ad libitum while ingesting the combination of 25-OH D and antioxidants/anti-inflammatories described herein. There may be a positive weight gain compared to eating a calorie controlled diet.

"Ascorbic Acid" and "Vitamin C" are used interchangeably throughout the specification and claims.

"Basal diet" means that the feed supplies the poultry with sufficient vitamins and minerals so that the poultry are vitamin and mineral replete.

"25-OH-D3+antioxidants/anti-inflammatories" means the combination of 25-OH D3, vitamin E, carotenoids of this invention (see next paragraph) and ascorbic acid, administered in addition to a diet which provides sufficient vitamins and minerals so that the person is not suffering a vitamin or mineral deficiency or insufficiency, at a dosage range as set forth in the specification. Optionally, and preferably, additional bio-active ingredients, selected from the group consisting of: Vitamin D, Vitamin B2, Vitamin B6, Niacin, Pantothenic Acid, Folic Acid, Biotin, Zinc, Copper, Manganese, Selenium and combinations thereof are added to the 25-OHD3, vitamin E, canthaxanthin and ascorbic acid combination.

"Carotenoids of this invention" means at least one of: lycopene, astaxanthin, cryptoxanthin, beta-carotene, lutein, zeaxanthin and canthaxanthin. Most preferred are at least one of: lycopene, astaxanthin, lutein, and zeaxanthin. Often, lutein and zeaxanthin are administered together.

1. Ovarian Problems

It has been found in accordance with this invention, that the use of a nutraceutical, food supplement or pharmaceutical composition comprising 25-OH D3, vitamin E, one or more carotenoids of this invention and ascorbic acid can specifically contribute to ovarian health. Use of the nutraceutical, food supplement or pharmaceutical of this invention can lessen, reduce, ameliorate or eliminate each of these conditions associated with polycystic ovary syndrome.

Poultry, and in particular laying hens are a recognized experimental model for human ovarian health. See, e.g. Johnson et al 2013 "The hen as a model of ovarian cancer" Nature.com/reviews/cancer 13: 432-436; and Walzem et at 2014 "Obesity-Induced Dysfunction in Female Reproduction: Lessons from Birds and Mammals"*Adv. Nutr* 5:199-206. Thus the data collected in the poultry study are applicable to humans.

1. Polycystic Ovary Syndrome Symptoms:

Women with polycystic ovary syndrome often experience symptoms such as one or more of: obesity, insulin resistance, hypertriglyceridemia, increased circulating concentrations of ceramide and non-esterified fatty acids (NEFAs), and systemic inflammogens, including IL-1β. It has been found that the combination of 25-OH D3, Vitamin C, Vitamin E and a carotenoid of this invention can ameliorate these symptoms.

Thus, another aspect of this invention is the use of the combination of 25-OH D3, Vitamin C, Vitamin E and one or more carotenoids selected from the group consisting of: lycopene, astaxanthin, cryptoxanthin, beta-carotene, and canthaxanthin for at least one of the uses selected from the group consisting of:

preventing human polycystic ovary syndrome;
treating human polycystic ovary syndrome;
delaying the onset of polycystic ovary syndrome; and
ameliorating a symptom of polycystic ovary syndrome.

Another aspect of this invention is a method of treating human polycystic ovary syndrome, ameliorating a symptom of polycystic ovary syndrome, or delaying the onset of polycystic ovary syndrome in a person at risk of developing the syndrome, comprising:

administering to a person who has polycystic ovary syndrome or who is at risk of developing polycystic ovary syndrome an effective amount of a combination comprising:
25-hydroxyvitamin D3, Vitamin C, Vitamin E, and one or more carotenoids selected from the group consisting of: lycopene, astaxanthin, cryptoxanthin, beta-carotene, lutein, zeaxanthin and canthaxanthin. In a preferred method, the aforementioned person is administered one or more carotenoids selected from the group consisting of: lycopene, astaxanthin, cryptoxanthin, and lutein.

2. Metabolic Problems

Metabolic problems associated with hyperphagia and which can be lessened, reduced or eliminated through use of the feed/premix of this invention include:

a) clearance of non-esterified fatty acids
b) amelioration of plasma dyslipidemia (triglycerides, sphingomyelin, and ceramide)
c) amelioration of triglyceride and ceraminde accumulation in the liver, leg, breast muscle, and heart
d) suppression the tissue pro-inflammatory IL-1β production and plasma IL-6 concentration
e) cardiac protection and enhanced cardiac function through the up-regulation of the phosphorylation of STAT-3 (signal transducer and activator of transcription 3) in the heart.
f) suppression of the infiltration of immune cells into the heart
g) decreasing the incidence of ascites.

These above-mentioned observed improved conditions result in a lowering of mortality rate, improved insulin signaling, reduced lipotoxic development and systemic inflammation, and activation of cardio-protective mechanisms against fuel-overload induced cardiac pathogenesis.

3. Cardio-Vascular Problems

Birds in a flock can experience a "sudden death". "Sudden Death" means that the individual bird died without showing previous signs or illness or trauma. Birds appear healthy, but die rapidly with a short period of wing beating and leg movement, during which they frequently flip onto their backs. They also may be found dead on their sides or breasts. There are no specific gross lesions. Recent studies indicate that dead birds have lesions in cardiomyocytes and subendocardial Purkinje cells, and this may help in diagnosis.

We investigated this phenomenon further, as detailed in Example 3, in flocks fed ad libitum and a restricted diet, with or without the combination of 25-OH D3 and antioxidants/anti-inflammatories. Some of our results are set forth below.

It has been found, in accordance with this invention, that in In birds fed ad libitum, sudden death birds which had been fed with 25-OH-D3+antioxidants/anti-inflammatories had higher body weight, but lower relative liver, abdominal fat, and heart weight. In the birds with sudden death, ad libitum feeding caused cardiac adaptive hypertrophy; and some of the hypertrophic growth may develop pathologically into ventricle dilation. As a result, the heart requires a higher contractility to maintain pumping function to meet the need of blood supply for oxygen delivery to the peripheral tissues. This condition may have caused heart failure.

Importantly, we found that 25-OH-D3+antioxidants/anti-inflammatories decreased cardiac pathogenic progression and thereby the incidence of heart failure in birds fed ad libitum. Thus another aspect of this invention is the use of 25-OH-D3+antioxidants/anti-inflammatories to reduce the amount of cardiac problems that can lead to cardiac failure.

In both restricted and ad libitum fed birds, birds with 25-OH-D3+antioxidants/anti-inflammatories exhibited less adaptive hypertrophic growth, supporting the hypothesis that most excessive fuels may be partitioned to the muscle, and thereby, hypertrophic growth of the heart for increased pumping function cannot meet the need of oxygen supply for higher growth rate (muscle) and thus may provoke cardiac arrhythmia and failure.

25-OH-D3+antioxidants/anti-inflammatories inclusion was seen to have the following effects:

decreased the incidence of cardiac morbidities (dilation, pericardial effusion, rupture) observed in necropsies of in the dead birds.
Decreased the amount of irregular incidence of ECG patterns
Decreased arrhythmia of broiler hens fed ad libitum
ameliorated sudden death induced by cardiac morbidities
ameliorated cardiac fibrosis in hens fed ad libitum.
ameliorated chronic systemic inflammation in hens fed ad libitum.
ameliorated cardiac cell apoptosis in hens with restricted or ad libitum feed intake.

Thus, the 25OH D3+antioxidants can protect the cardiovascular system.

Use of supplemental 25-OH D3 and antioxidants/anti-inflammatories ameliorated deleterious effects associated has various cardiovascular benefits. Thus this invention includes use of 25-OH D3 and antioxidants/anti-inflammatories for at least one cardiovascular benefit selected from the group consisting of:

a) clearance of non-esterified fatty acids;
b) amelioration of plasma dyslipidemia (triglycerides, sphingomyelin, and ceramide);
c) amelioration of triglyceride and ceraminde accumulation in the liver, leg, muscles, and heart;
d) suppression of the tissue pro-inflammatory IL-1β production and plasma IL-6 concentration;
e) cardiac protection and enhanced cardiac function through the up-regulation of the phosphorylation of STAT-3 (signal transducer and activator of transcription 3) in the heart;
f) suppression of the infiltration of immune cells into the heart;
g) decreasing the incidence of ascites;
h) decreasing the incidence of death due to cardiovascular problems;
i) decreasing the incidence of cardiac morbidities (dilation, pericardial effusion, rupture);
j) decreasing the amount of irregular incidence of ECG patterns;
k) decreasing the occurrence of arrhythmias;
l) ameliorating cardiac fibrosis;
m) ameliorating chronic systemic inflammation; and
n) ameliorating cardiac cell apoptosis
o) improved insulin resistance and/or blood glucose regulation.

3. Doses

In one aspect of this invention the combination of 25-OH D3 and the antioxidants/anti-inflammatories of this invention are administered to vitamin replete rather than vitamin deficient individuals. The vitamin replete status is preferably due to the a balanced diet which supplies at least the minimum amount of vitamins and minerals for the person. The combination of this invention is thus preferably used in addition to the basic diet.

25-OH D3:

25-OH D3 is present in a daily dosage is from 1 µg to 50 µg, preferably about 5 µg and 25 rig. In some embodiments 10 µg is used.

Vitamin E:

The amount in a daily dosage can range from 5-750 mg/day, preferably from 10-600 mg/day and more preferably from 100-500 mg per day. In some embodiments, 400 mg is used.

Ascorbic Acid:

The amount of ascorbic acid can range from 1-1000 mg/day, preferably from 100-1000 mg/day. More preferably it can range from 200-1000 mg/day.

Lycopene:

The amount of lycopene can range from 1-150 mg/day; preferably 5-35 mg/day.

Astaxanthin:

The amount of astaxanthin can range from 1-150 mg/day, preferably 2-50 mg/day, more preferably 5-20 mg/day.

β-Cryptoxanthin

The amount of β-cryptoxanthin can range from 1-100 mg/day; preferably from 2-30 mg/day; and more preferably from 5-15 mg/day.

Beta-Carotene

The amount of beta-carotene can range from 1-100 mg/day; preferably from 2-20 mg/day and more preferably 5-15 mg/day.

Zeaxanthin:

The amount of zeaxanthin can range from 1-60 mg/day; preferably 2-20 mg/day; and more preferably 3-10 mg/day.

Lutein: The amount of lutein can range from 1 to 100 mg/day, preferably from 2-20 mg/day, and more preferably from 6-12 mg/day.

Canthaxanthin:

The amount of canthaxanthin should not exceed 30 mg/day.

Representative Daily Formula 1:
25-OH D3: 5-25 µg, preferably 10 µg
Vitamin E 400 mg
Ascorbic acid: 100-1000 mg, preferably 200-1000
Cryptoxanthin: 0.10 mg Representative Daily Formula #2:
25-OH D3: 5-25 µg, preferably 12.5 µg
Vitamin E: 10 mg
Ascorbic acid: 100-1000 mg, preferably 200-1000
Lutein 6-12 mg
(optional) Zeaxanthin: 6 mg Representative Daily Formula #3
25-OH D3: 5-25 µg, preferably 12.5 µg
Vitamin E: 200-600 mg, preferably 300-500 mg
Ascorbic acid: 100-1000 mg, preferably 200-1000
Lycopene: 20 mg Representative Daily Formula #4
25-OH D3: 5-25 µg, preferably 10 µg
Vitamin E: 200-600 mg, preferably 300-500 mg
Ascorbic acid: 100-1000 mg, preferably 200-1000
Astaxanthin: 20 mg Representative Daily Formula #5
25-OH D3: 5-25 µg, preferably 12.5 µg
Vitamin E: 200-600 mg, preferably 300-500 mg
Ascorbic acid: 100-1000 mg, preferably 200-1000
Beta Carotene: 10 mg Preferred ratios include the following

| Vit E | Vit C | Carotenoid |
|-------|-------|------------|
| 1-10  | 1-10  | 1          |
| 1-20  | 1-10  | 1          |
| 1-20  | 1-20  | 1          |
| 1-10  | 1-20  | 1          |

Optional Additional Ingredients

To each of the nutraceutical, food supplement or pharmaceutical composition listed above, at least one of the additional ingredients may be added. Preferably at least one, and more preferably more than one of the following ingredients are added. In other embodiments, all the following ingredients are added:

Vitamin D3—The amount of vitamin D3 can range from 1-100 µg/day; preferably from 1-50 µg/day and more preferably 5-25 µg/day.

Vitamin B2: The amount of Vitamin B2 can range from 0.5-300 mg/day; preferably from 5-100 mg/day and more preferably 10-50 mg/day.

Niacin: The amount of Niacin can range from 1-300 mg/day; preferably from 5-100 mg/day and more preferably 10-50 mg/day.

Pantothenic acid: The amount of Pantothenic acid can range from 1-300 mg/day; preferably from 5-100 mg/day and more preferably 10-50 mg/day.

Folic acid: The amount of Folic acid can range from 50-100 µg/day; preferably from 400-800 µg/day and more preferably 400-600 µg/day.

Biotin: The amount of Biotin can range from 5 µg to 10 mg/day; preferably from 30 µg to-5 mg/day and more preferably 0.1-1 mg/day.

Zinc: The amount of Zinc can range from 1-40 mg/day; preferably from 5-40 mg/day and more preferably 10-20 mg/day.

Copper: The amount of Copper can range from 0.4-10 mg/day; preferably from 0.7-5 mg/day and more preferably 0.9-3 mg/day.

Manganese: The amount of Manganese can range from 1-10 mg/day; preferably from 1-5 mg/day and more preferably 1-3 mg/day.

Selenium: The amount of Selenium can range from 20-400 µg/day; preferably from 50-200 µg/day and more preferably 50-100 µg/day.

Premixes can be made to give the above-mentioned doses and preferred doses. One premix which forms part of this invention is formulated so that 1 gram of premix is added to one kilogram nutraceutical, food supplement or pharmaceutical composition, and that the resulting nutraceutical, food supplement or pharmaceutical composition contains the dosages described in any of the given dosages above. The amounts of the individual ingredients can, of course be varied so that one kilogram of premix is added to one metric ton of nutraceutical, food supplement or pharmaceutical composition and that the resulting feed contains the dosages described in any of the given dosages above. There are specific illustrations of this in the Examples, below.

Formulations

Another aspect of this invention relates to a nutraceutical composition comprising the combination of 25-OH D, Vitamin C, Vitamin E and at least one carotenoid according to this invention and a nutraceutically acceptable carrier.

The term "nutraceutical" as used herein includes: food products, foodstuffs, dietary supplements, nutritional supplements or a supplement composition for a food product or a foodstuff. Thus, in another embodiment the present invention relates to a nutraceutical wherein the nutraceutical is a food product, foodstuff, dietary supplement, nutritional supplement or a supplement composition for a food product or a foodstuff.

As used herein, the term "food product" refers to any food or suitable for consumption by humans. The food product may be a prepared and packaged food (e.g., mayonnaise, salad dressing, bread, or cheese food. As used herein, the term "foodstuff" refers to any substance fit for human consumption. The term "dietary supplement" refers to a small amount of a compound for supplementation of a human diet packaged in single or multiple dose units. Dietary supplements do not generally provide significant amounts of calories but may contain other micronutrients (e.g., vitamins or minerals). The term "nutritional supplement" refers to a composition comprising a dietary supplement in combination with a source of calories. In some embodiments, nutritional supplements are meal replacements or supplements (e.g., nutrient or energy bars or nutrient beverages or concentrates).

Food products or foodstuffs are, for example, beverages such as non-alcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks and milk and other dairy drinks such as for example yoghurt drinks, and diet drinks. In another embodiment food products or foodstuffs refer to solid or semi-solid foods comprising the composition according to the invention. These forms can include, but are not limited to baked goods such as cakes and cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yogurt and any other fat or oil containing foods, and food ingredients (e.g., wheat flour). The term "food products" or "foodstuffs" also includes functional foods and prepared food products, the latter referring to any pre-packaged food approved for human consumption.

Dietary supplements of the present invention may be delivered in any suitable format. In preferred embodiments, dietary supplements are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like.

The dietary supplement is preferably in the form of a tablet or capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of *Remington's Pharmaceutical Sciences* (Maack Publishing Co., Easton, Pa.).

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food e.g. enclosed in caps of food or beverage container for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, enhancers, colorants, sweeteners, flavorings, inert ingredients, and the like.

The following non-limiting Examples are presented to better illustrate the invention.

EXAMPLES

Example 1

A total of thirty 45-week-old broiler breeder hens (ROSS 308) were obtained from a commercial flock for the study. A basal broiler breeder laying diet was formulated as shown in Table 1. The calculated nutrient composition is shown in Table 2.

TABLE 1

Ingredient composition of the basal broiler breeder laying diets.

| Composition | %, w/w |
|---|---|
| Corn | 66.9 |
| Soybean meal | 22.2 |
| Oil fat | 1.67 |
| Ca Carbonate (ground oyster shell) | 6.36 |
| Dicalcium phosphate | 1.8 |
| Choline-Cl (70%) | 0.1 |
| Mineral Premix[1] | 0.1 |
| Copper sulfate | 0.05 |
| Vitamin Premix[2] | 0.1 |

[1]Mineral premix provided (per kg of diet for treatment groups 1, 2 and 3): Cu 18 mg; I 1.1 mg; Fe 80 mg; Mn 150 mg; Zn 125 mg; and Se 0.25 mg.
[2]Refer to Table 2 for further detail.

TABLE 2

Vitamin premix composition (provided per kg of diet)

| Vitamin | Treatments 1 and 2<br>1 = restricted feeding<br>2 = ad libitum feeding | Treatment 3<br>3 = ad libitum<br>feeding + 25-OH-D3 +<br>antioxidants/anti-<br>inflammatories |
|---|---|---|
| A (IU) | 10000 | 12000 |
| D3 (IU) | 2500 | 3000 |
| E (mg) | 100 | 150 |

TABLE 2-continued

Vitamin premix composition (provided per kg of diet)

| Vitamin | Treatments 1 and 2<br>1 = restricted feeding<br>2 = ad libitum feeding | Treatment 3<br>3 = ad libitum<br>feeding + 25-OH-D3 +<br>antioxidants/anti-<br>inflammatories |
|---|---|---|
| K3 (mg) | 3 | 5 |
| B1 (mg) | 3 | 5 |
| B2 (mg) | 8 | 14 |
| B6 (mg) | 6 | 8 |
| B12 (mg) | 0.03 | 0.03 |
| Niacin (mg) | 60 | 120 |
| Pantothenic acid (mg) | 18 | 30 |
| Folic acid (mg) | 1 | 4 |
| Biotin (mg) | 0.2 | 0.4 |
| C (ascorbic acid) (mg) | 0 | 150 |
| 25-OH-D3 (mcg) | 0 | 69 |
| Canthaxanthin (mg) | 0 | 6 |

TABLE 3

Calculated nutrient composition (%) of the basal broiler breeder laying diets.

| Composition | % w/w |
|---|---|
| Crude protein | 16 |
| Crude fat | 4.2 |
| Calcium | 3.1 |
| Sodium | 0.16 |
| Total Phosphorus | 0.64 |
| Total ME | 2910 kcal/kg |

Diet was supplemented with or without 25-OH D3 at 69 mcg/kg diet in combination with antioxidants/anti-inflammatories (vitamin E, ascorbic acid, canthaxanthin) and enriched levels of selected vitamins. Hens were randomly allocated to 3 treatment groups according to feeding regimen (restricted and ad libitum) as follows:
Basal diet—restricted feeding (140 g/day)
Basal diet—ad libitum feeding
Basal diet—ad libitum feeding+25-OH-D3 at 69 mcg/kg diet+antioxidants/anti-inflammatories They were individually-housed in wire cages placed in a controlled room with 14 h:10 h light:dark period and at a temperature of 25±3° C. Water was available ad libitum. The experimental period was lasted for 10 weeks. Three weeks after the feeding trial, some birds were used for relevant plasma parameter analyses. At the end of experiment, hens were euthanized and sacrificed for tissue sample collection for further studies: Necropsy of tissue morphology
Determination of lipid and sphingolipid profile—serum and tissues
Determination of tissue pro-inflammatory cytokines
Determination of insulin resistance
Collection of tibia for bone strength analysis
Harvesting heart (cardiomyopathy) and skeletal muscle (breast and thigh) for myopathy analyses.

Example 2

Results and Discussion

25-OH D3 and Antioxidants/Anti-Inflammatories Suppressed Adiposity and Abdominal Fat in Overfed Broiler Hens Breeder hens are capable of storing large quantities of excess energy (in the form of triglycerides) in the liver, adipose tissue and yolk of developing oocytes. Lipogenesis (i.e., the conversion of glucose to triglycerides) takes place primarily in the liver of birds and involves a series of linked, enzyme catalyzed reactions including glycolysis, the citric acid cycle and fatty acid synthesis. Hepatic lipogenesis is subject to both nutritional and hormonal control and is highly responsive to changes in the diet. Adipose tissue serves primarily as a storage site for lipid with little lipogenic activity. Differential lipogenic capacity of liver vs. adipose tissue in birds is a function of the expression of a key transcription factor, sterol regulatory element binding protein-1 (SREBP-1). The gene for SREBP-1 is highly expressed in the liver, but to a much lesser extent in adipose tissue. Moreover, the expression of a number of lipogenic enzyme genes such as fatty acid synthase, malic enzyme, acetyl CoA carboxylase, ATP citrate lyase and steroyl CoA desaturase 1 is directly influenced by SREBP-1.

Breeder hens fed ad libitum accreted more abdominal fat than those restricted fed. Dietary supplementation of 25-OHD3 and antioxidants/anti-inflammatories ameliorated the deleterious effect of ad libitum feeding on body and tissue weight, particularly on relative adipose tissue weight (adiposity) (Table 4). Tibial strength of ad libitum-fed hens was enhanced by 25-OH D3 and antioxidants/anti-inflammatories.

TABLE 4

25-OH D3 and antioxidants/anti-inflammatories on body weight, liver weight, abdominal fat weight and tibial strength of ad libitum-fed broiler breeder hens

|  | Restricted feeding | Ad libitum feeding | Ad libitum feeding + 25-OH-D3 + Antioxidants + anti-inflammatories | Pooled SEM[1] |
|---|---|---|---|---|
| Body weight (kg) | 3.67$^c$ | 4.60$^a$ | 4.04$^b$ | 0.26 |
| Liver weight (g) | 41.4$^b$ | 48.5$^a$ | 49.6$^a$ | 5.6 |
| Liver/body weight (%) | 1.14 | 1.06 | 1.23 | 0.18 |
| Abdominal fat weight (g) | 40.9$^c$ | 185.9$^a$ | 110.8$^b$ | 28.9 |
| Abdominal fat weight/body weight (%) | 1.10$^c$ | 4.01$^a$ | 2.74$^b$ | 0.70 |
| Tibial strength (kg/cm2) | 32.3$^b$ | 38.3$^{ab}$ | 44.3$^a$ | 3.57 |

$^{a-c}$Within a row, means without a common superscript differ (P < 0.05).
[1]Pooled standard error of the mean.

25-OH D3 and Antioxidants/Anti-Inflammatories Lowered Mortality and Improved Egg Production, Ovarian Morphology and Plasma 17β Estradiol Level Secretion of estradiol is the hallmark of successful ovulatory follicles. In addition to its role in triggering the preovulatory surge of gonadotropins, estradiol is an important intra-ovarian growth, differentiation, and survival factor. Inclusion of 25-OH D3 and antioxidants/anti-inflammatories reduced mortality and incidence of ovarian degeneration and ovarian-tumor-like morphology, increased egg production and sustained plasma estradiol levels in birds under ad libitum feed intake.

25-OH D3 and Antioxidants/Anti-Inflammatories Ameliorated Impaired Glucose Clearance and Insulin Sensitivity Dietary inclusion of 25-OH D3 and antioxidants/anti-inflammatories improves insulin resistance as evidenced by ameliorating fasting plasma glucose and non-esterifed fatty acid level in overfed hens for 10 weeks (Table 6). In glucose clearance test, lean hens showed a very sharp clearance rate between 30-60 min after glucose infusion, and conversely obese hens had a very sluggish clearance rate between 30-90 min (FIG. 1). In insulin secretion, obese hens showed a higher plasma insulin level under fasting status and after glucose infusion when compared to lean hens (FIG. 1). Both glucose clearance and glucose-induced insulin secretion were corrected by 25-OH D3 and antioxidants/anti-inflammatories inclusion in overfed hens for 3 weeks (FIG. 1).

TABLE 5

25-OH D3 and antioxidants/anti-inflammatories on plasma glucose, non-esterified fatty acid (NEFA) and insulin of ad libitum-fed broiler breeder hens

| | Restricted feeding | Ad libitum feeding | Ad libitum feeding + 25-OH-D3 ++ antioxidants/ anti-inflammatories | Pooled SEM[1] |
|---|---|---|---|---|
| After 3 weeks of feeding | | | | |
| Plasma glucose (mg/dL) | 181.5 | 202.5 | 188.5 | 11.9 |
| Plasma NEFA (μmole/mL) | 0.21[b] | 0.35[a] | 0.25[b] | 0.05 |
| After 10 weeks of feeding | | | | |
| Plasma glucose (mg/dL) | 180.6[b] | 212.6[a] | 195.6[b] | 12.7 |
| Plasma NEFA (μmole/mL) | 0.35[b] | 0.44[a] | 0.33[b] | 0.05 |
| Fasting plasma insulin | 1.38 | 1.15 | 1.59 | 0.21 |
| Glucose-induced insulin | 2.66a | 1.97b | 2.46a | 0.36 |

[a-b]Within a row, means without a common superscript differ ($P < 0.05$).
[1]Pooled standard error of the mean.

25-OH D3 and Antioxidants/Anti-Inflammatories Ameliorated Dyslipidemia

Ad libitum-fed hens elevated plasma triglyceride, ceramide and sphingomyelin levels. However, supplementation of combined 25-OH D3 and antioxidants/anti-inflammatories lowered the level of these lipid metabolites in the plasma of ad libitum-fed hens (Table 6).

TABLE 6

25-OH D3 and antioxidants/anti-inflammatories on plasma triacyglycerol, ceramide and sphingomyelin of ad libitum-fed broiler breeder hens

| | Restricted feeding | Ad libitum feeding | Ad libitum feeding + 25-OH-D3 ++ antioxidants/ anti-inflammatories | Pooled SEM[1] |
|---|---|---|---|---|
| After 3 weeks of feeding | | | | |
| Plasma triacyglycerol (mg/mL) | 15.6 | 17.4 | 14.5 | 2.9 |
| Plasma ceramide (nmole/mL) | 11.5[b] | 18.2[a] | 13.5[b] | 2.83 |
| Plasma sphingomyelin (μmole/mL) | 0.14[b] | 0.28[a] | 0.16[b] | 0.05 |
| After 10 weeks of feeding | | | | |
| Plasma triacyglycerol (mg/mL) | 12.75[b] | 15.2[a] | 11.5[b] | 2.2 |
| Plasma ceramide (nmole/mL) | 8.1[b] | 12.3[a] | 8.8[b] | 1.65 |
| Plasma sphingomyelin (μmole/mL) | 0.15[b] | 0.22[a] | 0.12[b] | 0.05 |

[a-b]Within a row, means without a common superscript differ ($P < 0.05$).
[1]Pooled standard error of the mean.

25-OH D3 and Antioxidants/Anti-Inflammatories Reduced Accumulation of Tissue Triglyceride and Ceramide Content Accumulation of triglyceride and ceramide in the liver, heart and leg muscles was lower in hens fed supplemental 25-OH D3 and antioxidants/anti-inflammatories than in those fed ad libitum (Table 7).

TABLE 7

25-OH D3 and antioxidants/anti-inflammatories on tissue triacyglycerol and ceramide content of ad libitum-fed broiler breeder hens

|  | Restricted feeding | Ad libitum feeding | Ad libitum feeding + 25-OH-D3 + Antioxidants + anti-inflammatories | Pooled SEM[1] |
|---|---|---|---|---|
| Triacyglycerol (mg/g tissue) |  |  |  |  |
| Liver | 69.0$^b$ | 94.8$^a$ | 79.8$^a$ | 10.6 |
| Heart | 33.1$^b$ | 55.6$^a$ | 45.6$^a$ | 6.8 |
| Breast muscle | 15.6 | 18.0 | 17.4 | 0.05 |
| Leg muscle | 30.2$^c$ | 52.3$^a$ | 41.2$^b$ | 6.6 |
| Ceramide (mg/g tissue) |  |  |  |  |
| Liver | 174.5$^b$ | 287.9$^a$ | 235.0$^a$ | 52.7 |
| Heart | 17.5$^c$ | 30.2$^a$ | 23.5$^b$ | 2.4 |
| Breast muscle | 2.25 | 2.91 | 2.52 | 0.54 |
| Leg muscle | 4.12$^b$ | 7.12$^a$ | 6.01$^a$ | 0.85 |

$^{a-b}$Within a row, means without a common superscript differ ($P < 0.05$).
[1]Pooled standard error of the mean.

Figure 2:
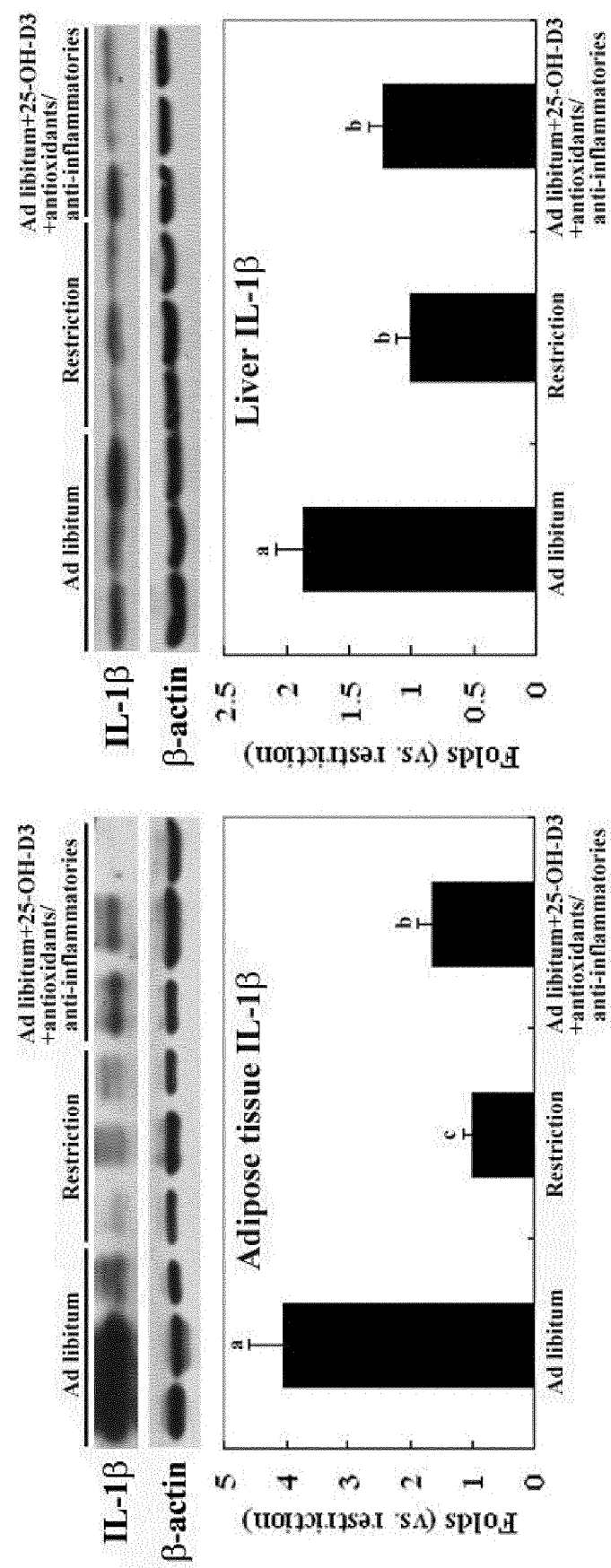
FIG. 2 shows tissue interleukin-1β contents and plasma IL-6 levels of broiler breeder hens in response to ad libitum feed intake in combination with 25-OH D3 and antioxidants/anti-inflammatories. Tissues and blood samples were collected after 10 weeks of the feeding trial. Means with different superscript letters are significantly different (P<0.05), n=3.

25-OH D3 and antioxidants/anti-inflammatories depressed tissue proinflammatory IL-1β Production and Plasma IL-6 Concentrations in Overfed Broiler Hens Obesity-associated inflammation was ameliorated by dietary 25-OH D3 and antioxidants/anti-inflammatories supplementation as evidenced by suppressed circulating IL-6 levels and IL-1β production in adipose tissue, liver, leg and breast muscle, and heart (FIG. 2).

25-OH D3 and Antioxidants/Anti-Inflammatories Ameliorated Lipotoxicity in Broiler Breeder Hens Fed Ad Libitum A central complication of obesity is the development of insulin resistance, which is when insulin is incapable of eliciting postprandial nutrient storage in its primary target tissues, skeletal muscle and liver. Without wishing to be bound by theory, it appears that two probable mechanisms may explain how increased adipose stores affect overall insulin sensitivity throughout the body, contributing to the down regulation of insulin signaling in peripheral tissues.

Firstly, the delivery of nutrients to cells or tissues is in excess of their storage capacities and thus this leads to the generation of metabolites that inhibit insulin action. Of particular importance, lipid derivatives, such as triacylglycerol and ceramide, have been shown to inhibit specific insulin signaling intermediates, thus blocking postprandial glucose uptake and/or glycogen synthesis. In the case of broiler breeder females being fed ad libitum, the persistent accumulation of these metabolites in peripheral tissues likely contributes to a sustained state of insulin resistance throughout the hen and of lipotoxic development. Secondly, increased adiposity induces a chronic inflammatory state characterized by elevated circulating levels of pro-inflammatory cytokines produced from adipocytes or from macrophages infiltrating the fat pad. These inflammatory mediators have been shown to antagonize insulin signaling directly, and also to induce catabolic processes, thus further increasing the delivery of nutrient metabolites to insulin-responsive organs.

Overall, excess supply of glucose leading to the formation of excess saturated fatty acids and therefore accumulation of lipids in non-adipose tissues elevates the cellular levels of -active lipids (sphingolipids) that inhibit the signaling pathways implicated in metabolic regulation together with activated inflammatory responses and lipotoxic development. In particular, ceramide is a putative intermediate linking both excess nutrients (i.e., saturated fatty acids) and inflammatory cytokines to the induction of insulin resistance. Moreover, ceramide is toxic in a variety of different cell types and is capable of damaging the heart, pancreas and vasculature. Moreover, 25-hydroxy D3 and antioxidants/anti-inflammatories were effective in ameliorating the deleterious effect of metabolic and endocrine dysregulations and pro-inflammatory responses resulting from increased adiposity occurring in broiler breeder hens fed to satiation.

25-OH D3 and Antioxidants/Anti-Inflammatories Ameliorate Cardiac Morbidities, Ascites, and Inflammation in Overfed Broiler Hens The heart may become dysfunctional due to excess lipid accumulation. That ad libitum feeding promoted triglyceride accumulation in the heart suggested that increased cardiac fatty acid availability is adaptively esterified into triglyceride. In addition, ceramide content of the heart was also increased as a result of ad libitum feeding. Ceramide is a cardiotoxin in lipotoxic cardiomyopathy, which elicited inflammatory responses as evidenced by more cardiac infiltration of immune cells. (Table 9).

TABLE 8

25-OH D3 and antioxidants/anti-inflammatories on cardiac responses of ad libitum-fed broiler breeder hens

|  | Restricted feeding | Ad libitum feeding | Ad libitum feeding + 25-OH-D3 + antioxidants + anti-inflammatories | Pooled SEM[1] |
|---|---|---|---|---|
| Heart weight (g) | 14.5$^b$ | 19.2$^a$ | 17.3$^a$ | 1.8 |
| Heart/body weight (%) | 0.40 | 0.47 | 0.43 | 0.17 |
| Heart septum (HS) weight (g) | 2.73 | 3.01 | 2.83 | 0.57 |
| HS weight/heart weight (%) | 18.7 | 14.6 | 15.7 | 3.9 |
| Right atrium (RA) wall weight (g) | 1.20$^b$ | 1.97$^a$ | 1.72$^{ab}$ | 0.38 |
| RA wall weight/heart weight (%) | 8.2 | 9.6 | 9.6 | 1.9 |
| Right ventricle (RV) wall weight (g) | 0.95$^b$ | 1.51$^a$ | 1.73$^a$ | 0.27 |
| RV wall weight/heart weight (%) | 6.3$^b$ | 7.5$^{ab}$ | 9.4$^a$ | 1.5 |
| Left atrium (LA) wall weight (g) | 1.17$^b$ | 2.26$^a$ | 2.02$^a$ | 0.43 |
| LA wall weight/heart weight (%) | 12.2 | 11.1 | 10.9 | 3.1 |
| Left ventricle (LV) wall weight (g) | 3.78$^b$ | 4.45$^a$ | 4.65$^a$ | 0.34 |

TABLE 8-continued

25-OH D3 and antioxidants/anti-inflammatories on cardiac responses of ad libitum-fed broiler breeder hens

|  | Restricted feeding | Ad libitum feeding | Ad libitum feeding + 25-OH-D3 + antioxidants + anti-inflammatories | Pooled SEM[1] |
|---|---|---|---|---|
| LV wall weight/heart weight (%) | 25.5[a] | 21.7[b] | 25.8[ab] | 2.4 |
| Incidence of transudate within pericardium (heart/total) | 1/7 | 5/10 | 3/10 | |
| Incidence of heart ventricle dilation (heart/total) | 1/7 | 6/10 | 3/10 | |
| Incidence of ascites (hen/total) | 0/7 | 3/10 | 1/10 | |
| Cardiac immune cell count (cells/mm2) | 97.9[a] | 127.7[a] | 57.7[b] | 32.4 |

[a-b]Within a row, means without a common superscript differ (P < 0.05).
[1]Pooled standard error of the mean.

Cardiac hypertrophy represents clinically an adaptive response to increased workload on the heart. However, cardiac responses to neural and hormonal factors can also incite hypertrophic changes independent of increases in afterload or vascular resistance. Fuel overloading-induced cardiac compensatory growth occurred in broiler breeder hens (Table 8). Cardiac hypertrophy may become maladaptive and eventually develop into pathological conditions, leading to heart failure. These results supported the fact that lipotoxic development and hypertrophic growth in the heart tend to elicit inflammatory responses.

Figure 3:
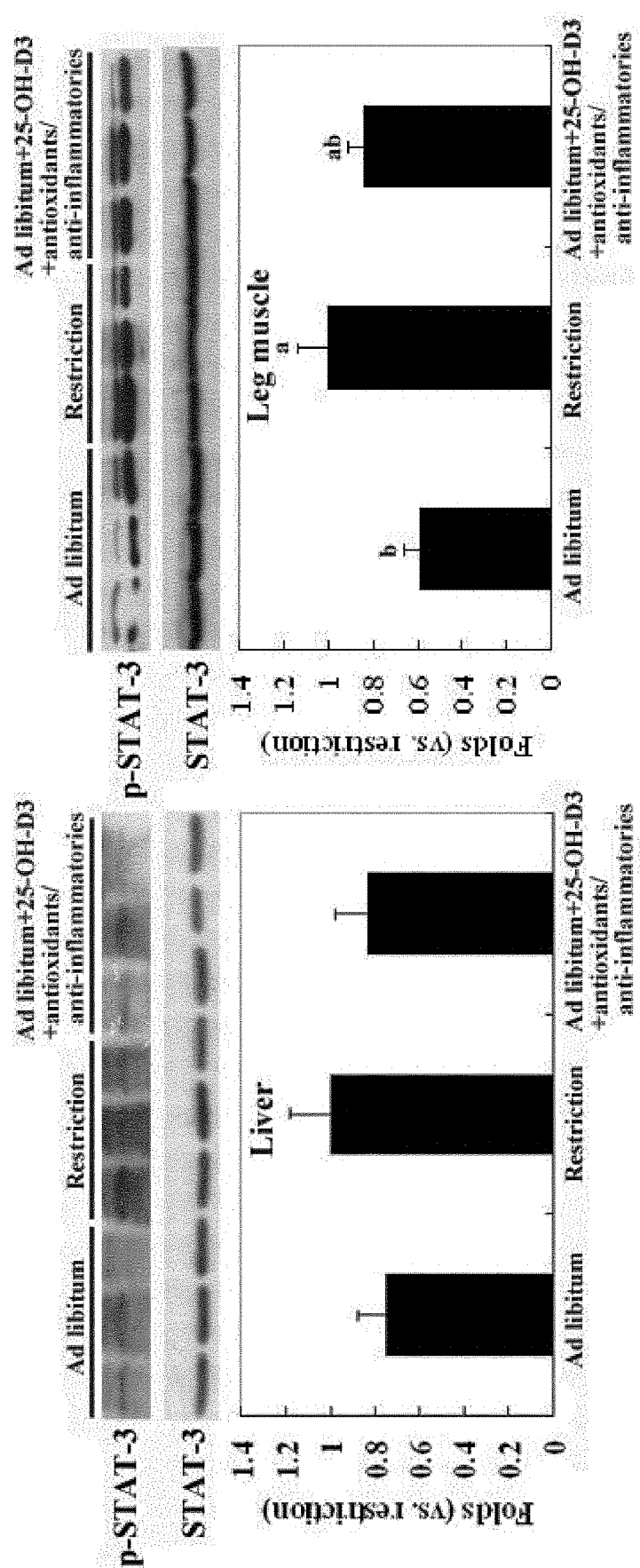
FIG. 3. shows tissue STAT-3 activation of broiler breeder hens in response to ad libitum feed intake in combination with 25-OH D3 and antioxidants/anti-inflammatories inclusion. Tissues and blood samples were collected after 10 weeks of the feeding trial. Means with different superscript letters are significantly different (P<0.05), n=3.
Figure 4:
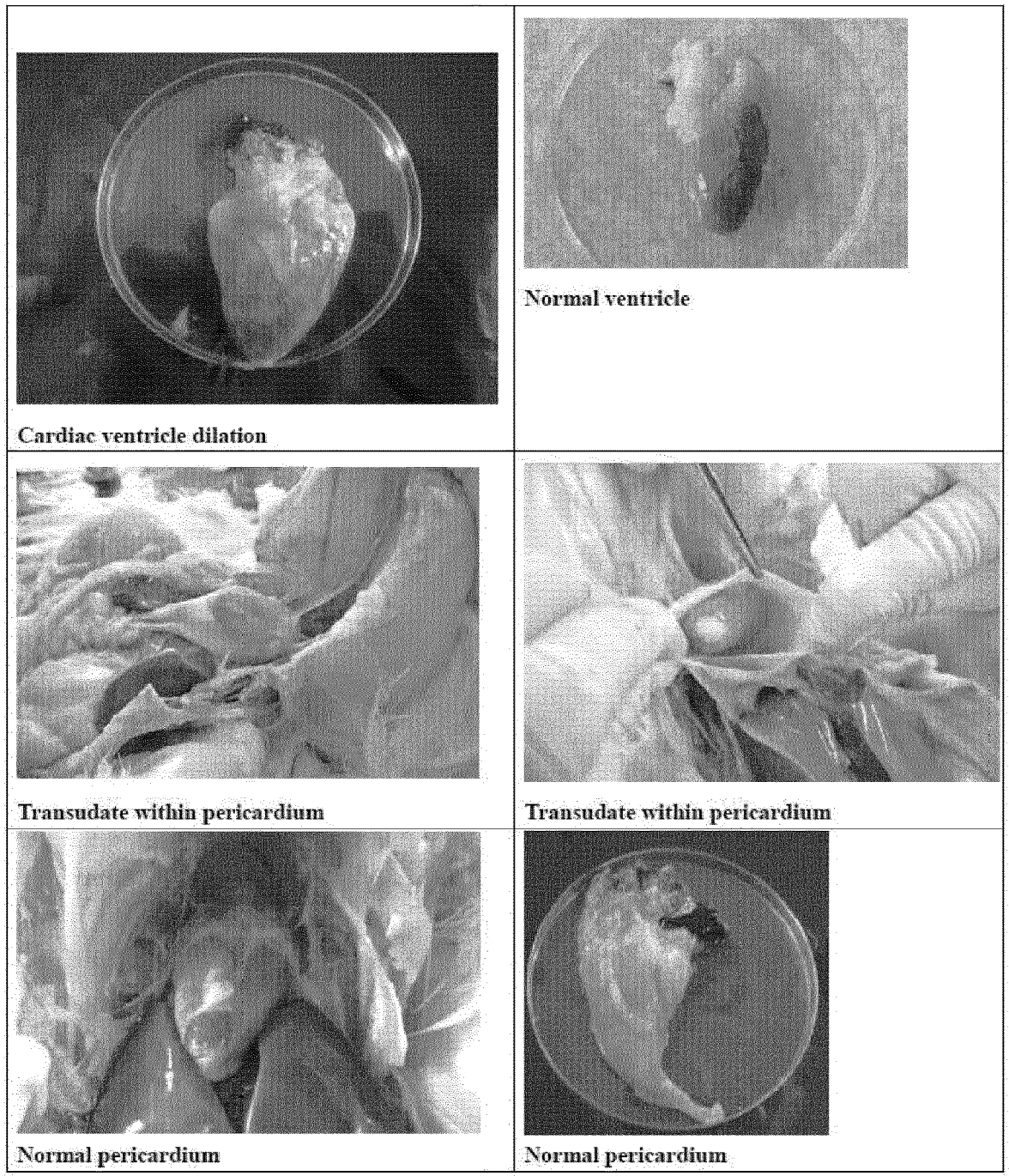
FIGS. 4-6 show pictures taken during the necropsy of broiler hens in response to ad libitum feed intake in combination with 25-OH D3 and antioxidants/anti-inflammatories inclusion. Hens were necropsied after 10 weeks of the feeding trial.
Figure 5:
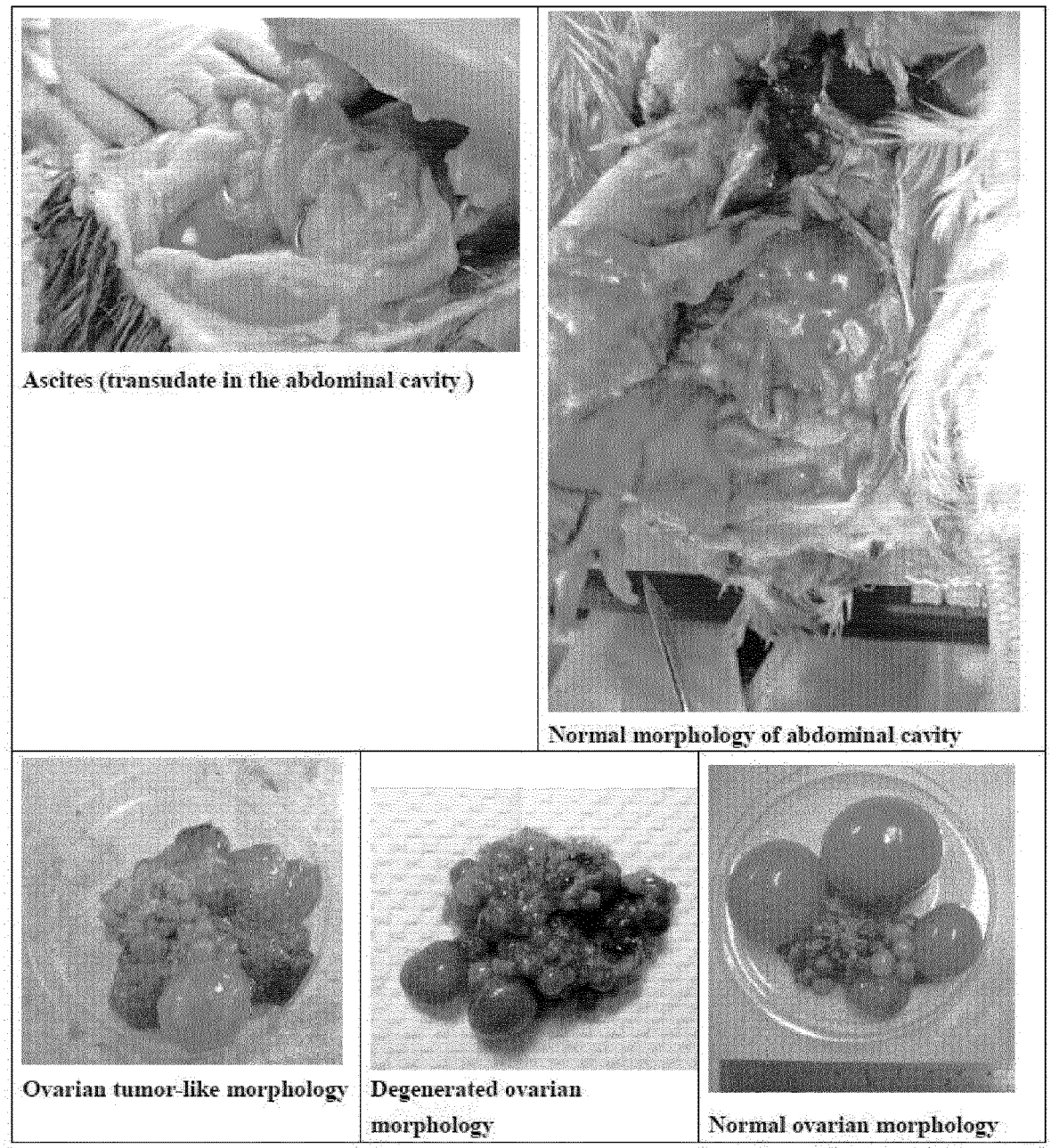
Figure 6:
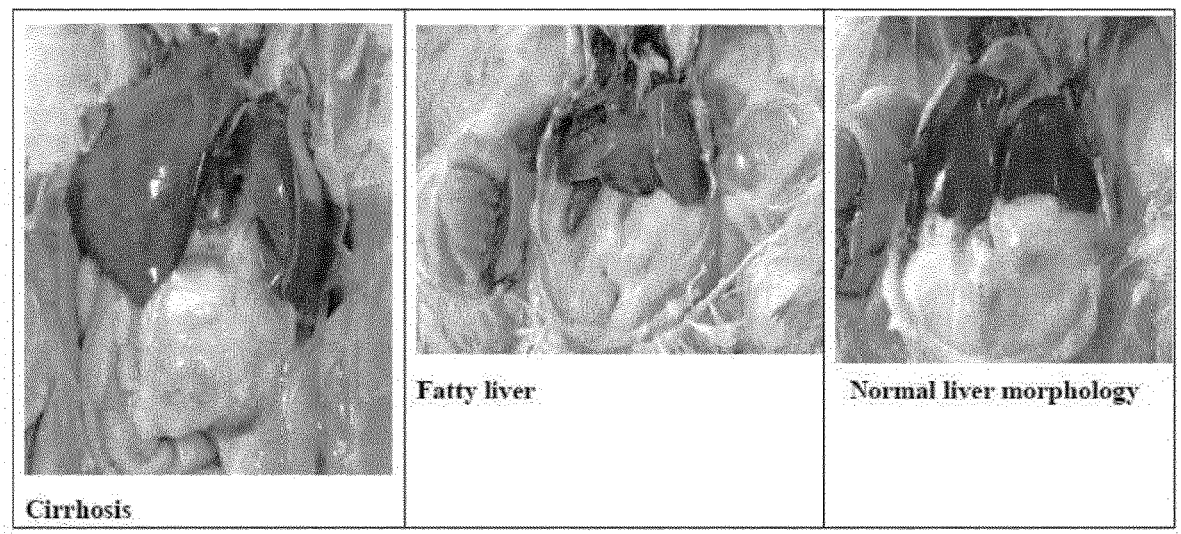

The cardioprotective role of phosphorylated STAT-3 (signal transducer and activator of transcription 3) is becoming increasingly clear in recent years. Interestingly, combined 25-OH D3 and antioxidants/anti-inflammatories induced greater activation of STAT-3 (i.e., phosphorylation of STAT-3) in the heart than restricted-fed breeder hens (FIG. 3), with the lowest activation being observed in ad libitum-fed broiler breeder hens. The incidence of transudate fluid within pericardium, heart ventricle dilation and ascites was alleviated in ad-libitum-fed breeder hens when supplemented with combined 25-hydroxy D3 and antioxidants/anti-inflammatories.

Example 3

Cardio-Myopathy Trial

Materials and Methods

A total of thirty 45-week-old broiler breeder hens (ROSS 308) were obtained from a commercial flock for the study. A basal broiler breeder laying diet was formulated as shown in Table 12. The calculated nutrient composition is shown in Table 13.

TABLE 12

Ingredient composition of the basal broiler breeder laying diets.

| Composition | %, w/w |
|---|---|
| Corn | 66.9 |
| Soybean meal | 22.2 |
| Oil fat | 1.67 |
| Calcium carbonate (ground oyster shell) | 6.36 |
| Dicalcium phosphate | 1.8 |
| Salt | 0.08 |
| Choline-Cl (70%) | 0.1 |
| Mineral premix[1] | 0.1 |

TABLE 12-continued

Ingredient composition of the basal broiler breeder laying diets.

| Composition | %, w/w |
|---|---|
| Cooper sulfate | 0.05 |
| Vitamin premix[2] | 0.1 |

[1]Mineral premix provided (per kg of diet for treatment groups 1, 2 and 3): Cu, 18 mg; I, 1.1 mg; Fe, 80 mg; Mn, 150 mg; Zn, 125 mg; and Se, 0.25 mg.
[2]Refer to Table 13, below for further detail.

TABLE 13

Vitamin premix composition (provided per kg of diet)

| Vitamin | Treatments 1 and 3<br>1 = restricted feeding<br>3 = ad libitum feeding | Treatments 2 and 4<br>2 = restricted feeding + 25-OH-D3 + antioxidants/anti-inflammatories<br>4 = ad libitum feeding + 25-OH-D3 + antioxidants/anti-inflammatories |
|---|---|---|
| A (IU) | 10000 | 12000 |
| D3 (IU) | 2500 | 3000 |
| E (mg) | 100 | 150 |
| K3 (mg) | 3 | 5 |
| B1 (mg) | 3 | 5 |
| B2 (mg) | 8 | 14 |
| B6 (mg) | 6 | 8 |
| B12 (mg) | 0.03 | 0.03 |
| Niacin (mg) | 60 | 120 |
| Pantothenic acid (mg) | 18 | 30 |
| Folic acid (mg) | 1 | 4 |
| Biotin (mg) | 0.2 | 0.4 |
| C (mg) | 0 | 150 |
| 25-OH-D3 (mcg) | 0 | 69 |
| Canthaxanthin (mg) | 0 | 6 |

TABLE 14

Calculated nutrient composition (%) of the basal broiler breeder laying diets.

| Composition | %, w/w |
|---|---|
| Crude protein | 16 |
| Crude fat | 4.2 |
| Calcium | 3.1 |

TABLE 14-continued

Calculated nutrient composition (%) of
the basal broiler breeder laying diets.

| Composition | %, w/w |
|---|---|
| Potassium | 0.44 |
| Sodium | 0.16 |
| Total phosphorus | 0.64 |
| Total ME | 2910 kcal/kg |

Diet was supplemented with or without Hy·D® at 69 mcg 25-OH-D3/kg diet in combination with antioxidants (ascorbic acid, canthaxanthin) and enriched levels of selected vitamins. Hens were randomly allocated to treatment groups according to feeding regimen (restricted and ad libitum) as follows:

1. Basal diet—restricted feeding (140 g/day)
2. Basal diet—restricted feeding+Hy·D® (25-OH-D3 at 69 mcg/kg diet)+antioxidants/anti-inflammatories
3. Basal diet—ad libitum feeding
4. Basal diet—ad libitum feeding+Hy·D® (25-OH-D3 at 69 mcg/kg diet)+antioxidants/anti-inflammatories Results:

TABLE 15

Effect of dietary supplementation of 25-OH-D3 + antioxidants/anti-inflammatories on egg production of broiler hens with restricted or ad libitum feed intake.

| | Restriction | | Restriction + 25-OH-D3 + antioxidant/anti-inflammatories | | Ad libitum | | Ad libitum + 25-OH-D3 + antioxidant/anti-inflammatories | |
|---|---|---|---|---|---|---|---|---|
| | Whole flock (n = 68) | Dead bird flock (n = 19) | Whole flock (n = 70) | Dead bird flock (n = 11) | Whole flock (n = 80) | Dead bird flock (n = 58) | Whole flock (n = 79) | Dead bird flock (n = 47) |
| PROD | 51.4 ± 2.5$^a$ | 47.2 ± 1.9$^a$ | 51.3 ± 2.7$^a$ | 40.2 ± 1.8$^b$ | 32.0 ± 2.9$^b$ | 43.4 ± 1.7$^{ab}$ | 34.8 ± 2.7$^b$ | 45.8 ± 2.1$^{ab}$ |
| YIELD | 129.0 ± 5.5$^b$ | 47.9 ± 2.5$^b$ | 143.2 ± 5.7$^a$ | 33.3 ± 1.9$^b$ | 41.1 ± 5.3$^d$ | 41.5 ± 2.1$^b$ | 54.7 ± 5.9$^c$ | 41.1 ± 2.0$^b$ |

PROD = Egg production rate (eggs/day/hen, %);
YIELD = Egg yield (eggs/hen)
Results were expressed with mean ± SEM.
Means with different superscript letters are significantly different within the same flock (P < 0.05)

Figure 7:
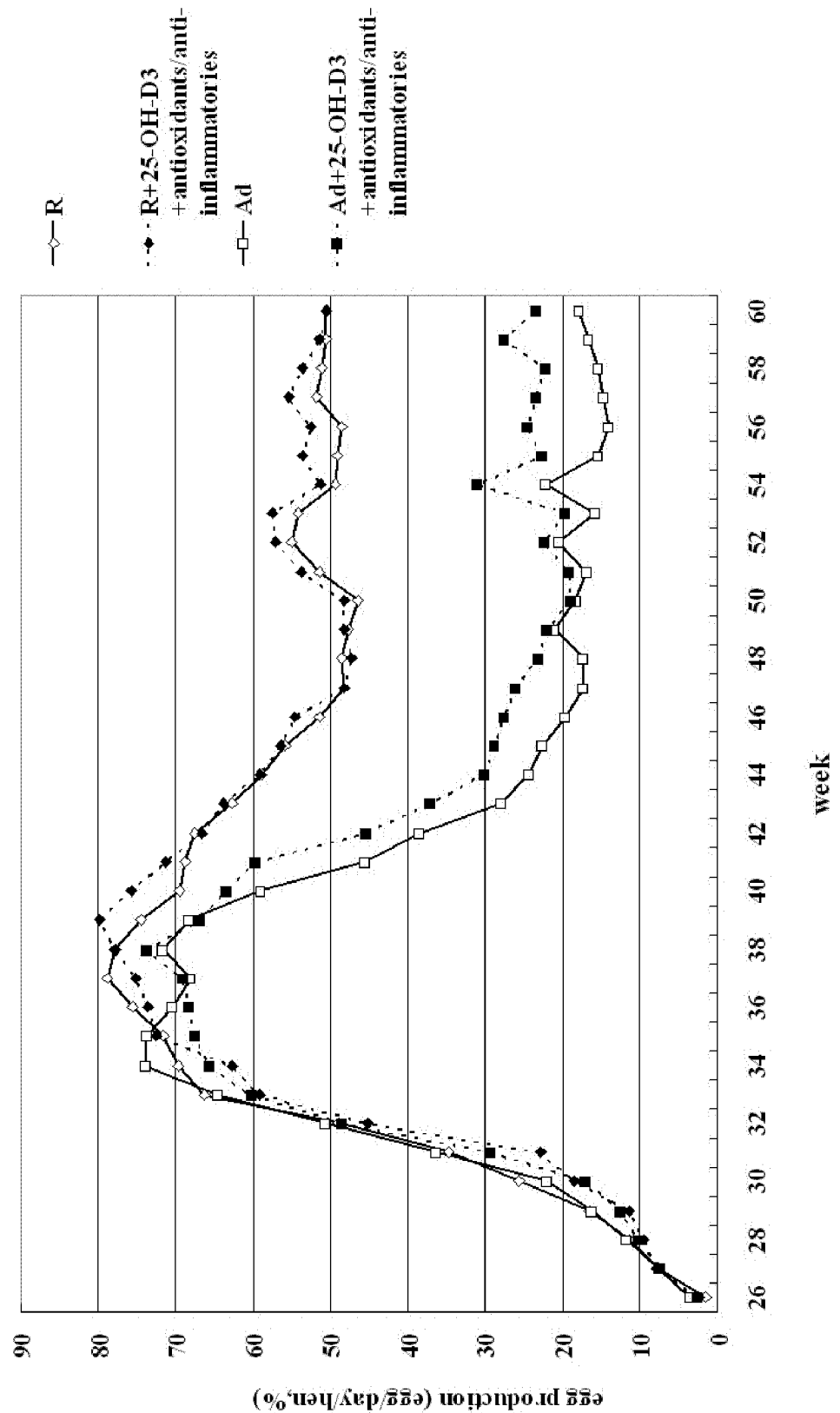
FIG. 7 shows the effect of dietary supplementation of 25-OH-D3+antioxidants/anti-inflammatories on egg production of broiler hens with restricted or ad libitum feed intake.

FIG. 7 shows the effect of dietary supplementation of 25-OH-D3+antioxidants/anti-inflammatories on egg production of broiler hens with restricted or ad libitum feed intake. From TABLE 15 and FIG. 7, it can be concluded that:

1. 25-OH-D3+antioxidants/anti-inflammatories improved total egg yield by promoting survival.
2. In dead birds, 25-OH-D3+antioxidants/anti-inflammatories had no effect on egg yield and egg production rate in bird fed ad libitum, but decreased egg yield and egg production rate in restricted birds. In the whole flock, however, 25-OH-D3+antioxidants/anti-inflammatories increased egg yield but not egg production rate.
3. These results suggested that 25-OH-D3+antioxidants/anti-inflammatories accelerated the progression into death in restricted birds that are susceptible to sudden death, and thus acting as a flock culler to exclude the sudden death-susceptible birds for longer survival and thereby reduced the flock maintenance cost.

TABLE 16

Effect of dietary supplementation of 25-OH-D3 + antioxidants/anti-inflammatories on mortality of broiler hens with restricted or ad libitum feed intake and body characteristics of the dead hens

| | Restriction (n = 19) | Restriction + 25-OH-D3 + antioxidant/anti-inflammatories (n = 11) | Ad libitum (n = 58) | Ad libitum ++ 25-OH-D3 + antioxidant/anti-inflammatories (n = 47) |
|---|---|---|---|---|
| Mortality (dead birds of the total) | 19/68 (26.47%) | 11/70 (15.71%) | 58/80 (72.5%) | 47/79 (59.49%) |
| Body weight of the dead birds (kg) | 3.91 ± 0.090$^c$ | 4.01 ± 0.084$^{bc}$ | 4.07 ± 0.083$^b$ | 4.37 ± 0.082$^a$ |

TABLE 16-continued

Effect of dietary supplementation of 25-OH-D3 + antioxidants/anti-inflammatories on mortality of broiler hens with restricted or ad libitum feed intake and body characteristics of the dead hens

|  | Restriction (n = 19) | Restriction + 25-OH-D3 + antioxidant/ anti-inflammatories (n = 11) | Ad libitum (n = 58) | Ad libitum ++ 25-OH-D3 + antioxidant/ anti-inflammatories (n = 47) |
|---|---|---|---|---|
| Liver weight of the dead birds (g) | $89.10 \pm 6.79^b$ | $99.27 \pm 7.92^{ab}$ | $105.52 \pm 5.48^a$ | $106.70 \pm 4.68^a$ |
| Relative liver weight of the dead birds (g/100 g BW) | $2.28 \pm 0.0016^d$ | $2.47 \pm 0.0020^b$ | $2.59 \pm 0.0011^a$ | $2.44 \pm 0.0009^c$ |
| Abdominal fat weight of the dead birds (g) | $60.45 \pm 4.56^b$ | $68.54 \pm 6.05^b$ | $148.64 \pm 8.45^c$ | $133.54 \pm 9.44^a$ |
| Relative abdominal fat weight of the dead birds (g/100 g BW) | $1.55 \pm 0.0013^d$ | $1.71 \pm 0.0016^c$ | $3.65 \pm 0.0014^a$ | $3.06 \pm 0.0009^b$ |
| Heart weight of the dead birds (g) | $18.12 \pm 0.81^c$ | $19.93 \pm 0.87^b$ | $23.66 \pm 0.96^a$ | $22.29 \pm 0.86^a$ |
| Relative heart weight of the dead birds (g/100 g BW) | $0.46 \pm 0.00023^c$ | $0.50 \pm 0.00021^b$ | $0.58 \pm 0.00024^a$ | $0.51 \pm 0.00018^b$ |

Results were expressed with mean ± SEM.
Means with different superscript letters are significantly different (P < 0.05)

Figure 8:
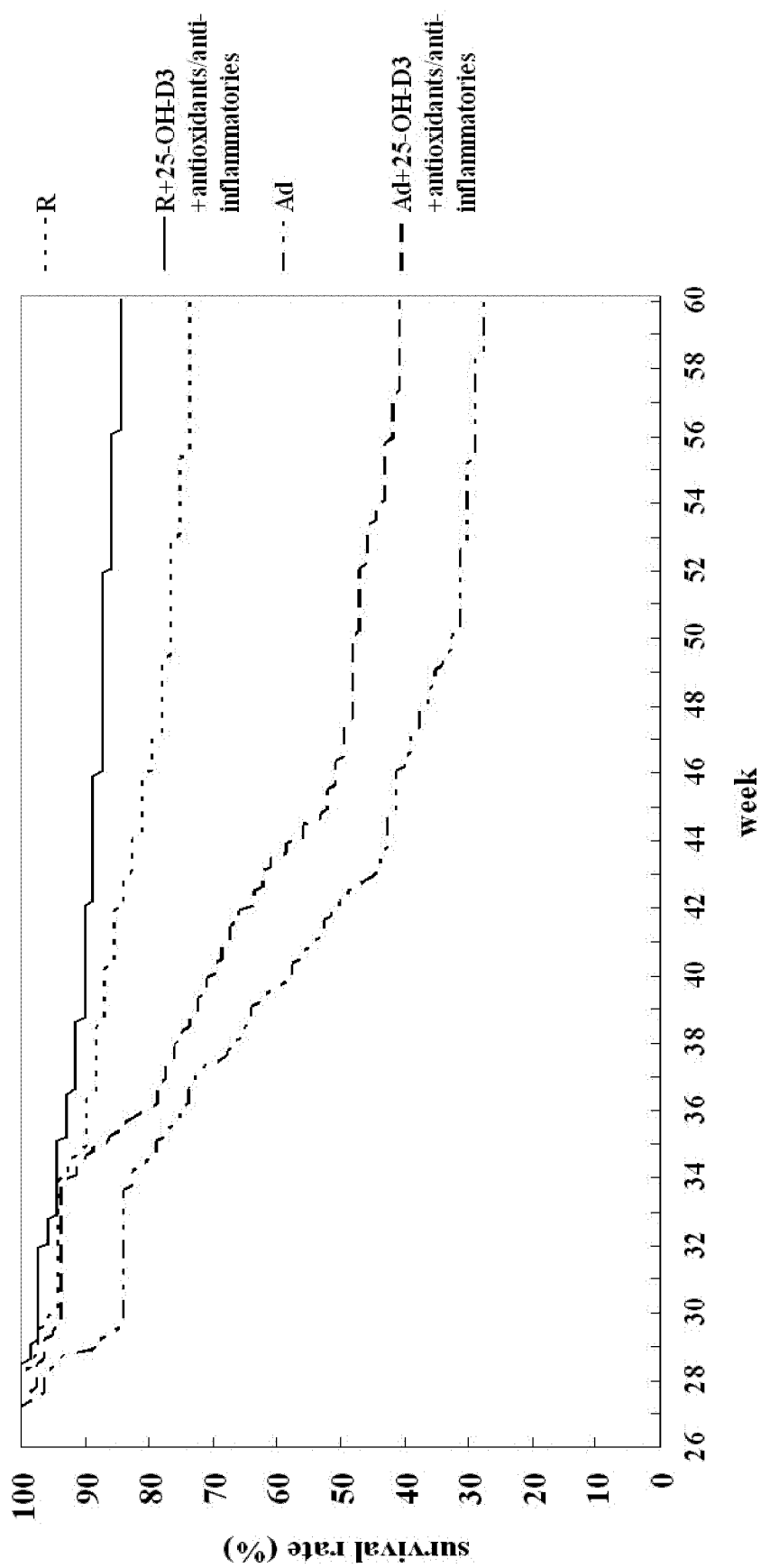
FIG. 8 shows the effect of dietary supplementation of 25-OH-D3+antioxidants/anti-inflammatories on the survival rate of broiler hens with restricted or ad libitum feed intake.

FIG. 8 shows the effect of dietary supplementation of 25-OH-D3+antioxidants/anti-inflammatories on the survival rate of broiler hens with restricted or ad libitum feed intake From Table 16 and FIG. 8 it can be concluded that:
1. 25-OH-D3+antioxidants/anti-inflammatories improved bird survival rate.
2. In birds fed ad libitum, dead birds with 25-OH-D3+ antioxidants/anti-inflammatories had higher body weight, but lower relative liver, abdominal fat, and heart weight, suggesting that most excessive fuels may be partitioned to the muscle, and thereby, adaptive hypertrophic growth of the heart for increased pumping function cannot meet the need of oxygen supply for higher growth rate (muscle) and thus may provoke cardiac arrhythmia and failure.

TABLE 17

Effect of dietary supplementation of 25-OH-D3 + antioxidants/anti-inflammatories on carcass characteristics at age of 35 and 50 weeks of broiler hens with restricted or ad libitum feed intake

|  | Restriction (n = 6) | Restriction + 25-OH-D3 + antioxidant/anti-inflammatories (n = 6) | Ad libitum (n = 6) | Ad libitum + 25-OH-D3 + antioxidant/anti-inflammatories (n = 6) |
|---|---|---|---|---|
| Body wt (kg): |  |  |  |  |
| at 35 wks | $3.57 \pm 0.19^b$ | $3.66 \pm 0.15^b$ | $4.32 \pm 0.27^a$ | $4.36 \pm 0.33^a$ |
| at 50 wks | $3.78 \pm 0.21^b$ | $3.83 \pm 0.23^b$ | $4.62 \pm 0.34^a$ | $4.71 \pm 0.38^a$ |
| Liver wt (g): |  |  |  |  |
| at 35 wks | $55.35 \pm 4.42^b$ | $57.37 \pm 2.27^b$ | $98.45 \pm 4.76^a$ | $83.37 \pm 4.17^b$ |
| at 50 wks | $58.67 \pm 3.84^b$ | $59.75 \pm 4.67^b$ | $72.56 \pm 5.14^{a*}$ | $68.45 \pm 3.42^{b*}$ |
| Relative liver wt (g/100 g BW, %): |  |  |  |  |
| at 35 wks | $1.55 \pm 0.06^d$ | $1.57 \pm 0.11^b$ | $2.28 \pm 0.10^a$ | $1.91 \pm 0.09^b$ |
| at 50 wks | $1.55 \pm 0.05$ | $1.56 \pm 0.14$ | $1.57 \pm 0.13^*$ | $1.45 \pm 0.07^*$ |
| Abdominal fat wt of the dead birds (g): |  |  |  |  |
| at 35 wks | $47.63 \pm 2.16^c$ | $50.57 \pm 3.64^c$ | $123.84 \pm 9.84^a$ | $95.47 \pm 8.12^b$ |
| at 50 wks | $51.24 \pm 2.38^c$ | $53.12 \pm 2.57^c$ | $147.62 \pm 8.55^{c*}$ | $112.47 \pm 9.01^c$ |

TABLE 17-continued

Effect of dietary supplementation of 25-OH-D3 + antioxidants/anti-inflammatories on carcass characteristics at age of 35 and 50 weeks of broiler hens with restricted or ad libitum feed intake

|  | Restriction (n = 6) | Restriction + 25-OH-D3 + antioxidant/anti-inflammatories (n = 6) | Ad libitum (n = 6) | Ad libitum + 25-OH-D3 + antioxidant/anti-inflammatories (n = 6) |
|---|---|---|---|---|
| Relative abdominal fat wt (g/100 g BW, %): | | | | |
| at 35 wks | $1.35 \pm 0.11^c$ | $1.38 \pm 0.06^c$ | $2.86 \pm 0.0^a$ | $2.19 \pm 0.03^b$ |
| at 50 wks | $1.36 \pm 0.12^c$ | $1.39 \pm 0.50^c$ | $3.20 \pm 0.06^{a*}$ | $2.39 \pm 0.08^{b*}$ |
| Heart wt (g): | | | | |
| at 35 wks | $12.69 \pm 0.38^b$ | $12.09 \pm 0.31^b$ | $17.33 \pm 0.65^a$ | $17.76 \pm 0.70^a$ |
| at 50 wks | $14.12 \pm 0.41^b$ | $13.88 \pm 0.0.36^b$ | $22.21 \pm 0.71^{a*}$ | $20.88 \pm 0.73^{a*}$ |
| Relative heart wt (g/100 g BW, %): | | | | |
| at 35 wks | $0.357 \pm 0\ 024^b$ | $0.331 \pm 0.011^b$ | $0.401 \pm 0\ 016^a$ | $0.414 \pm 0.046^{ab}$ |
| at 50 wks | $0.374 \pm 0.025^b$ | $0.362 \pm 0.024^b$ | $0.481 \pm 0.015^{a*}$ | $0.443 \pm 0.024^{ab}$ |

Results were expressed with mean ± SEM.
Means with different superscript letters are significantly different (P < 0.05)
*significant difference vs. age at 35 wks.

The low relative liver weight in ad libitum birds at age of 50 weeks appears to be due to ovarian regression developed and thus decreased estrogen secretion leading to decreased lipid synthesis in the liver for yolk deposition.

Figure 9:
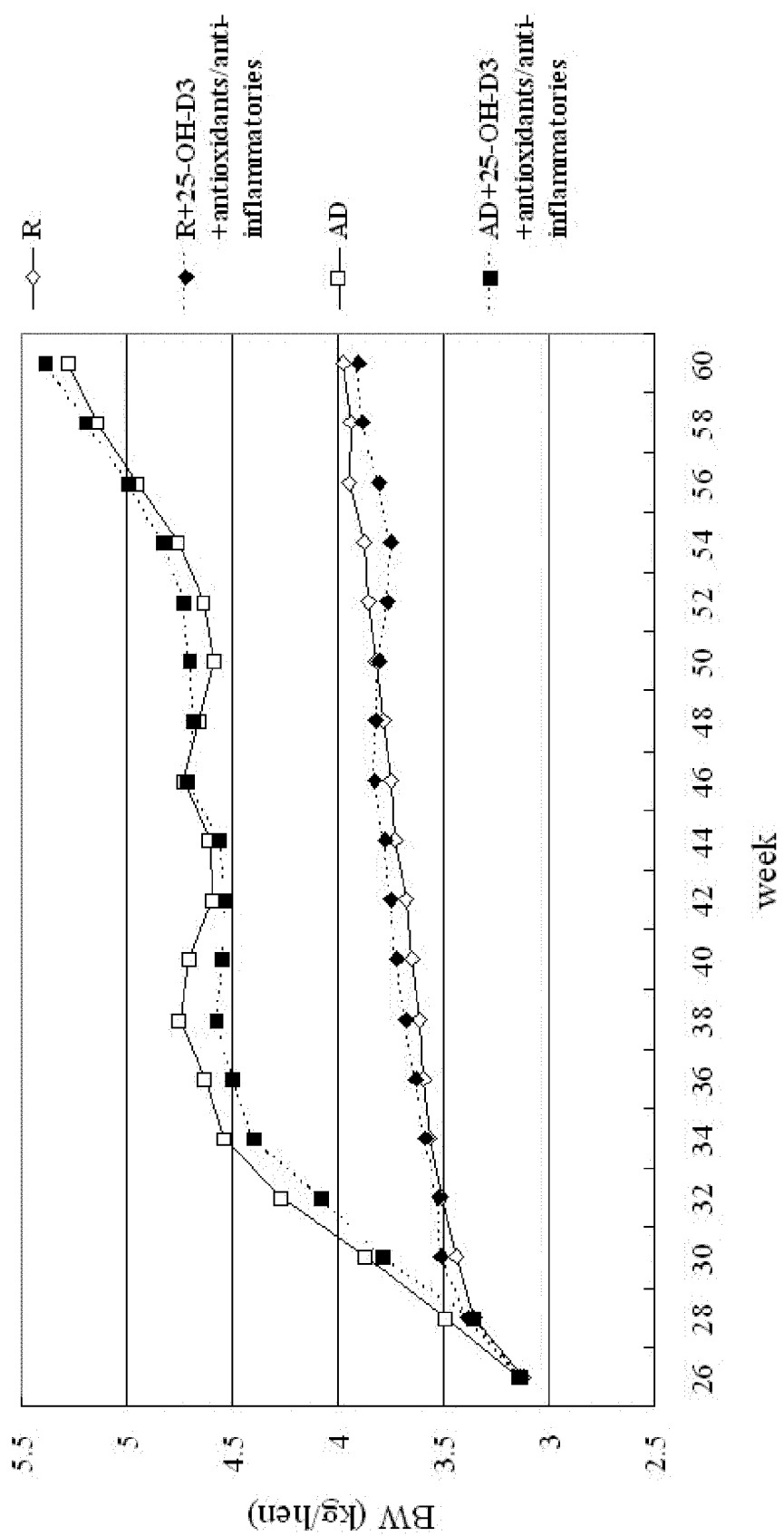
FIG. 9 shows the effect of dietary supplementation of 25-OH-D3+antioxidants/anti-inflammatories on body weight of broiler hens with restricted or ad libitum feed intake.

FIG. 9 shows the effect of dietary supplementation of 25-OH-D3+antioxidants/anti-inflammatories on body weight of broiler hens with restricted or ad libitum feed intake.

TABLE 18

Effect of dietary supplementation of 25-OH-D3 + antioxidants/anti-inflammatories on the cardiac morbidities of the dead hens with restricted or ad libitum feed intake

|  | Restriction (n = 19) | Restriction + 25-OH-D3 + antioxidant/anti-inflammatories (n = 11) | Ad libitum (n = 58) | Ad libitum + (25-OH-D3 + antioxidant/anti-inflammatories (n = 47) |
|---|---|---|---|---|
| Mortality (dead birds of the total) | 19/68 (26.47%) | 11/70 (15.71%) | 58/80 (72.5%) | 47/79 (59.49%) |
| Cardiac morbidities (birds of the death) | | | | |
| 1. hypertrophy | 6/19 | 0/11 | 20/58 | 14/47 |
| 2. ventricle dilation | 3/19 | 3/11 | 16/58 | 10/47 |
| 3. effusion in the pericardial cavity | 6/19 | 0/11 | 26/58 | 15/47 |
| 4. ascites | 2/19 | 0/11 | 7/58 | 5/47 |
| 5. myocardial rupture trauma | 1/19 | 0/11 | 6/58 | 4/47 |
| 1 + 3 | 2/19 | 0/11 | 10/58 | 7/47 |
| 2 + 3 | 2/19 | 1/11 | 11/58 | 6/47 |
| 1 + 4 | 2/19 | 0/11 | 3/58 | 0/47 |
| 3 + 4 | 1/19 | 0/11 | 2/58 | 1/47 |

TABLE 18-continued

Effect of dietary supplementation of 25-OH-D3 + antioxidants/anti-inflammatories on the cardiac morbidities of the dead hens with restricted or ad libitum feed intake

|  | Restriction (n = 19) | Restriction + 25-OH-D3 + antioxidant/anti-inflammatories (n = 11) | Ad libitum (n = 58) | Ad libitum + (25-OH-D3 + antioxidant/anti-inflammatories (n = 47) |
|---|---|---|---|---|
| 2 + 5 | 0/19 | 0/11 | 3/58 | 1/47 |
| 2 + 3 + 4 | 0/19 | 0/11 | 2/58 | 1/47 |

Results were exoressed as a ratio

Results were expressed as a ratio.

Figure 10:
FIG. 10 is a series of photos showing the gross morphology of the heart of dead hens with dietary supplementation of 25-OH-D3+antioxidants/anti-inflammatories under restricted or ad libitum feed intake.
Figure 10B:
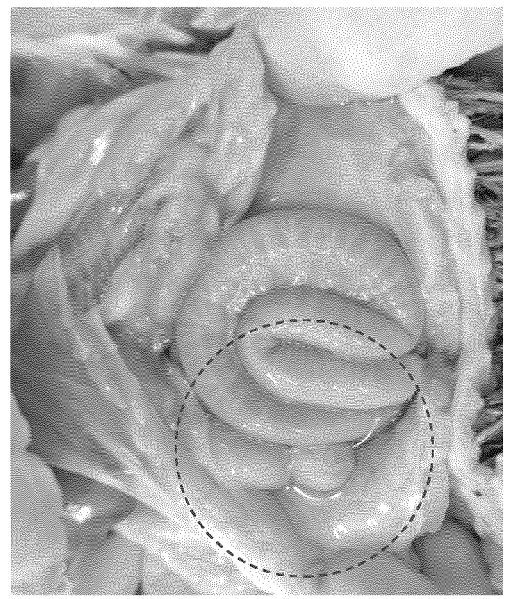
Figure 10C:
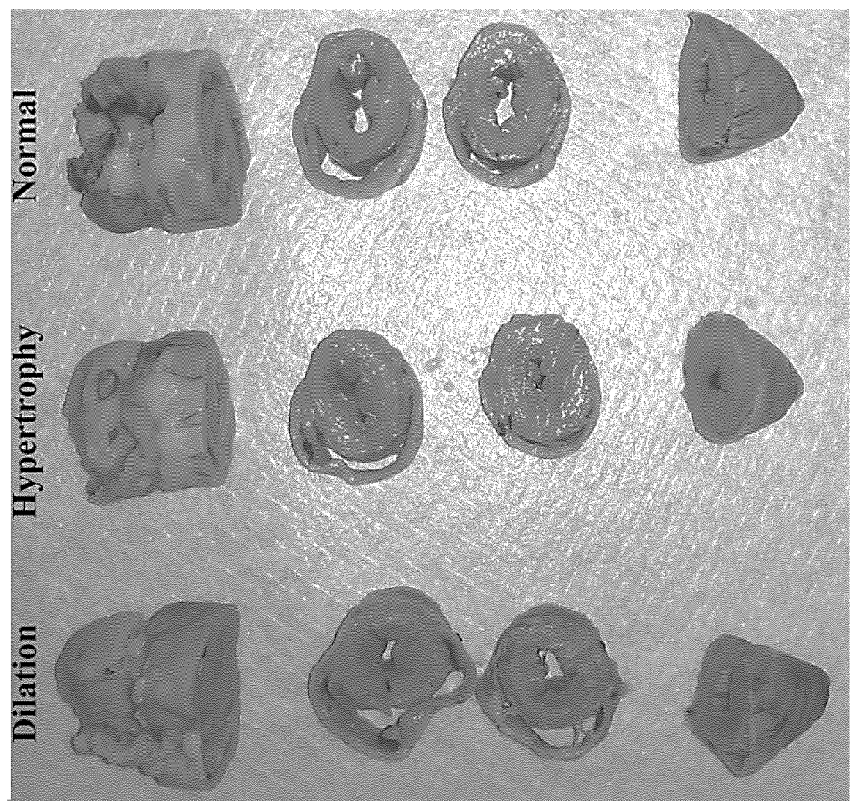
Figure 11:
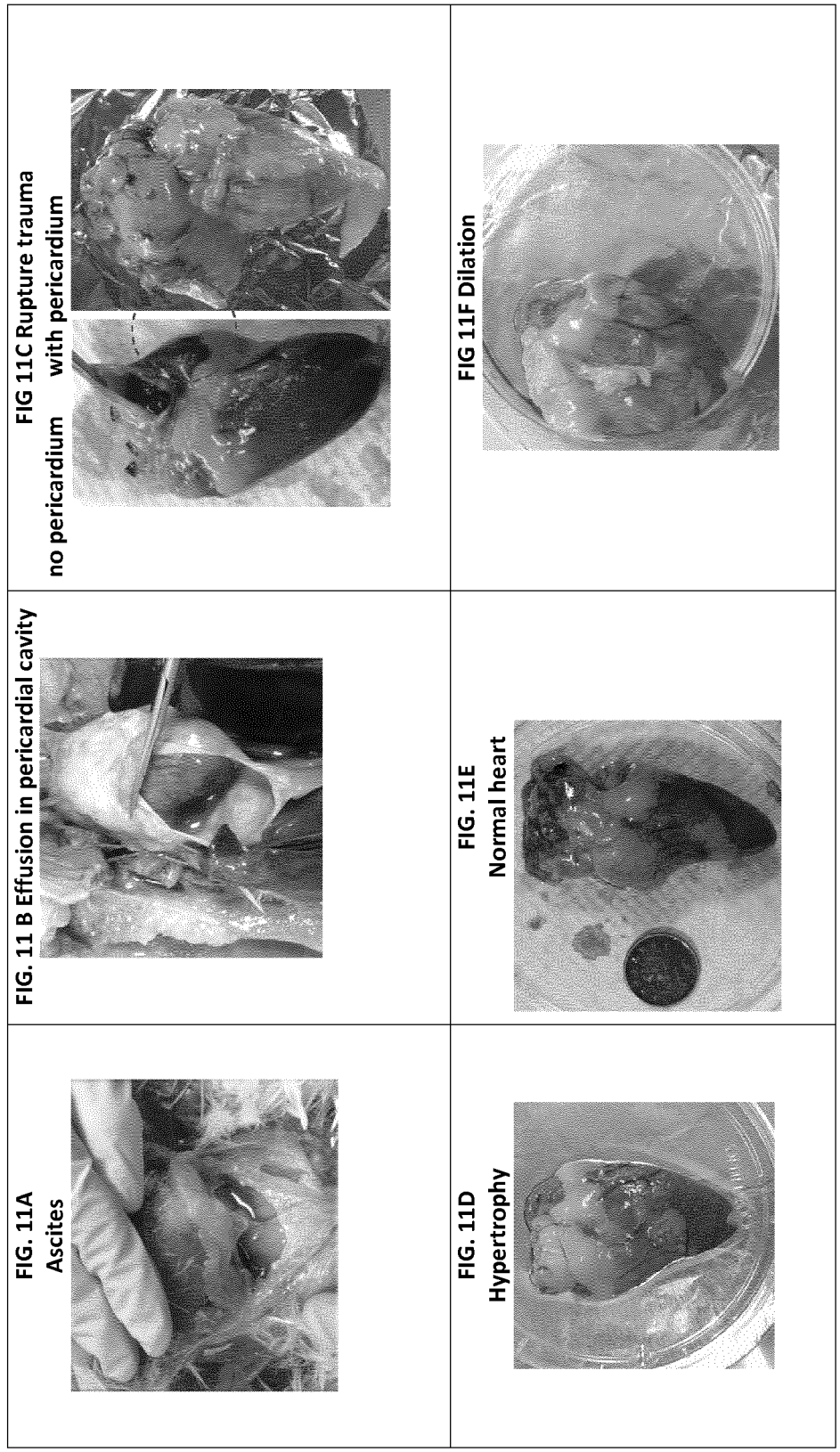
FIG. 11 is a series of photographs showing the gross morphology of the heart of dead hens with dietary supplementation of 25-OH-D3+antioxidants/anti-inflammatories under restricted or ad libitum feed intake

FIGS. 10-11 illustrate the gross morphology of the heart of dead hens with dietary supplementation of 25-OH-D3+antioxidants/anti-inflammatories under restricted or ad libitum feed intake.

Conclusions and annotations from Tables 17 and 18 and FIGS. 9-11:

1. Ad libitum feeding caused cardiac adaptive hypertrophy, and some of the hypertrophic growth may develop pathologically into ventricle dilation. As a result, the heart requires a higher contractility to maintain pumping function to meet the need of blood supply for oxygen delivery to the peripheral tissues and thus may provoke heart failure.
2. 25-OH-D3+antioxidants/anti-inflammatories decreased the incidence of cardiac morbidities (dilation, pericardial effusion, rupture) in the dead birds.
3. In both restricted and ad libitum fed birds, birds with 25-OH-D3+antioxidants/anti-inflammatories exhibited less adaptive hypertrophic growth. This supports the hypothesis that most excessive fuels may be partitioned to the muscle, and thereby, hypertrophic growth of the heart for increased pumping function cannot meet the need of oxygen supply for higher growth rate (muscle) and thus may provoke cardiac arrhythmia and failure.

25-OH-D3+antioxidants/anti-inflammatories decreased irregular incidence of ECG pattern (pattern D to G) and arrhythmia of broiler hens fed ad libitum and ameliorated sudden death induced by cardiac morbidities.

Figure 14:
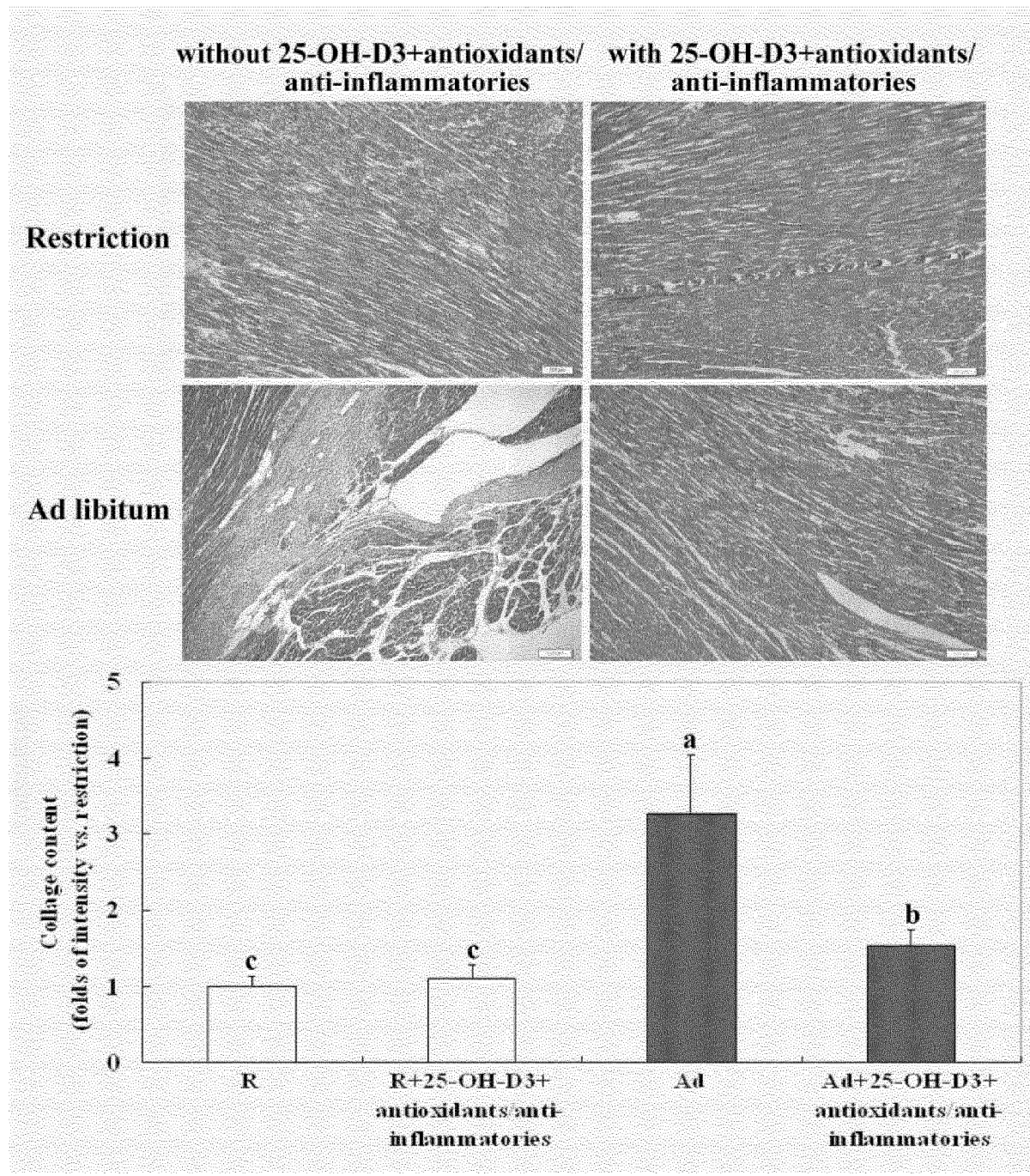
FIG. 14 shows photos and a graph demonstrating the effect of dietary supplementation of 25-OH-D3+antioxidants/anti-inflammatories on cardiac fibrosis of broiler hens with restricted or ad libitum feed intake. (at age of 35 weeks)

FIG. 14 shows the effect of dietary supplementation of 25-OH-D3+antioxidants/anti-inflammatories on cardiac fibrosis of broiler hens with restricted or ad libitum feed intake. (at age of 35 weeks) Means with letters over the bars are significantly different (P<0.05)

Conclusions and annotations from FIG. 14:

1. 25-OH-D3+antioxidants/anti-inflammatories ameliorated cardiac fibrosis in hens fed ad libitum.

Figure 15:
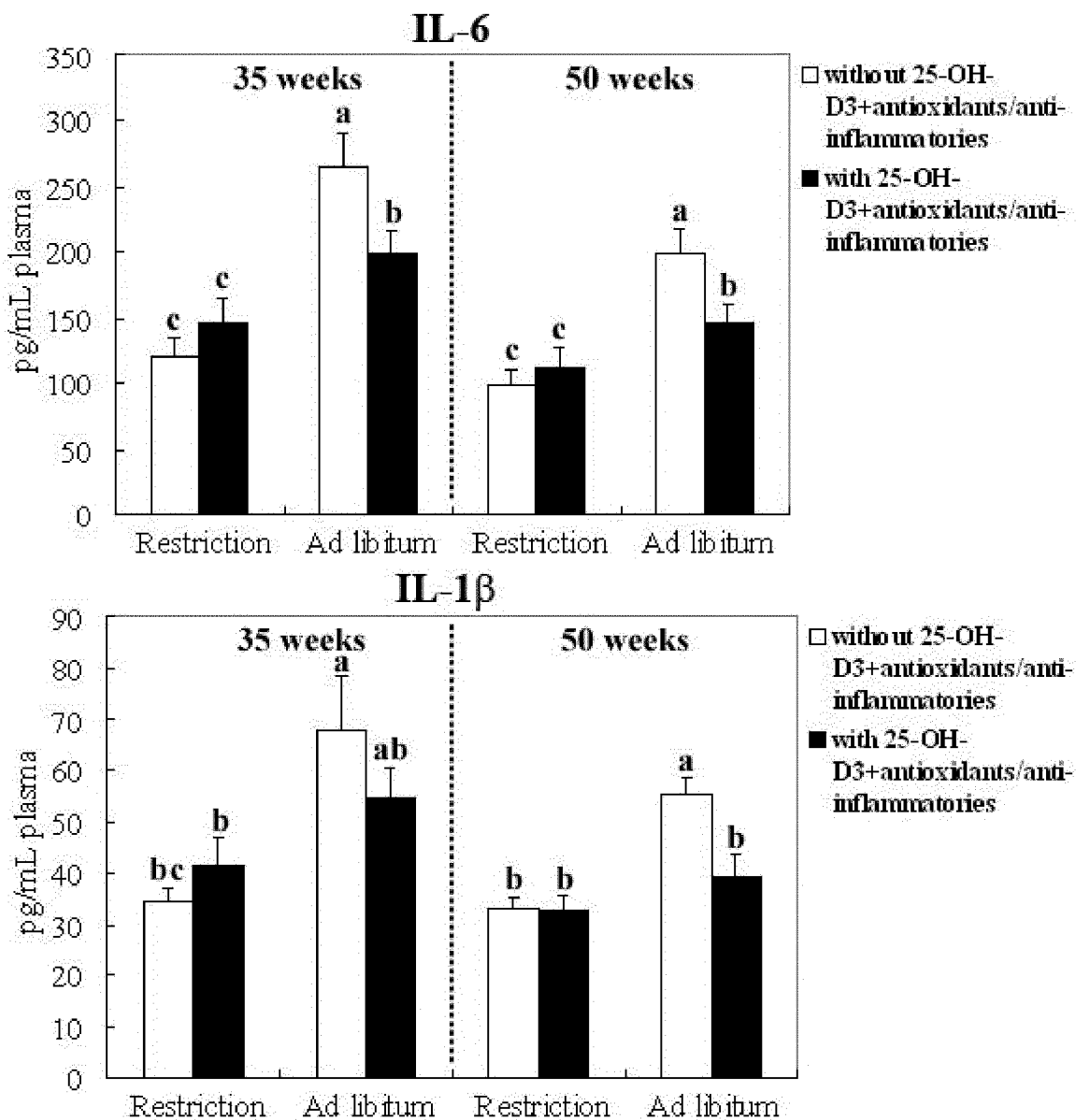
FIG. 15 are graphs showing the effect of dietary supplementation of 25-OH-D3+antioxidants/anti-inflammatories on plasma IL-6 and IL-1β concentration of broiler hens with restricted or ad libitum feed intake.

FIG. 15 shows the effect of dietary supplementation of 25-OH-D3+antioxidants/anti-inflammatories on plasma IL-6 (top graphs) and IL-1β concentration (lower graphs) of broiler hens with restricted or ad libitum feed intake. Results were expressed with mean±SEM (n=6). Means with different letters over the bars are significantly different (P<0.05)

Conclusions and annotations from FIG. 15:

25-OH-D3+antioxidants/anti-inflammatories ameliorated chronic systemic inflammation in hens fed ad libitum.

Figure 16:
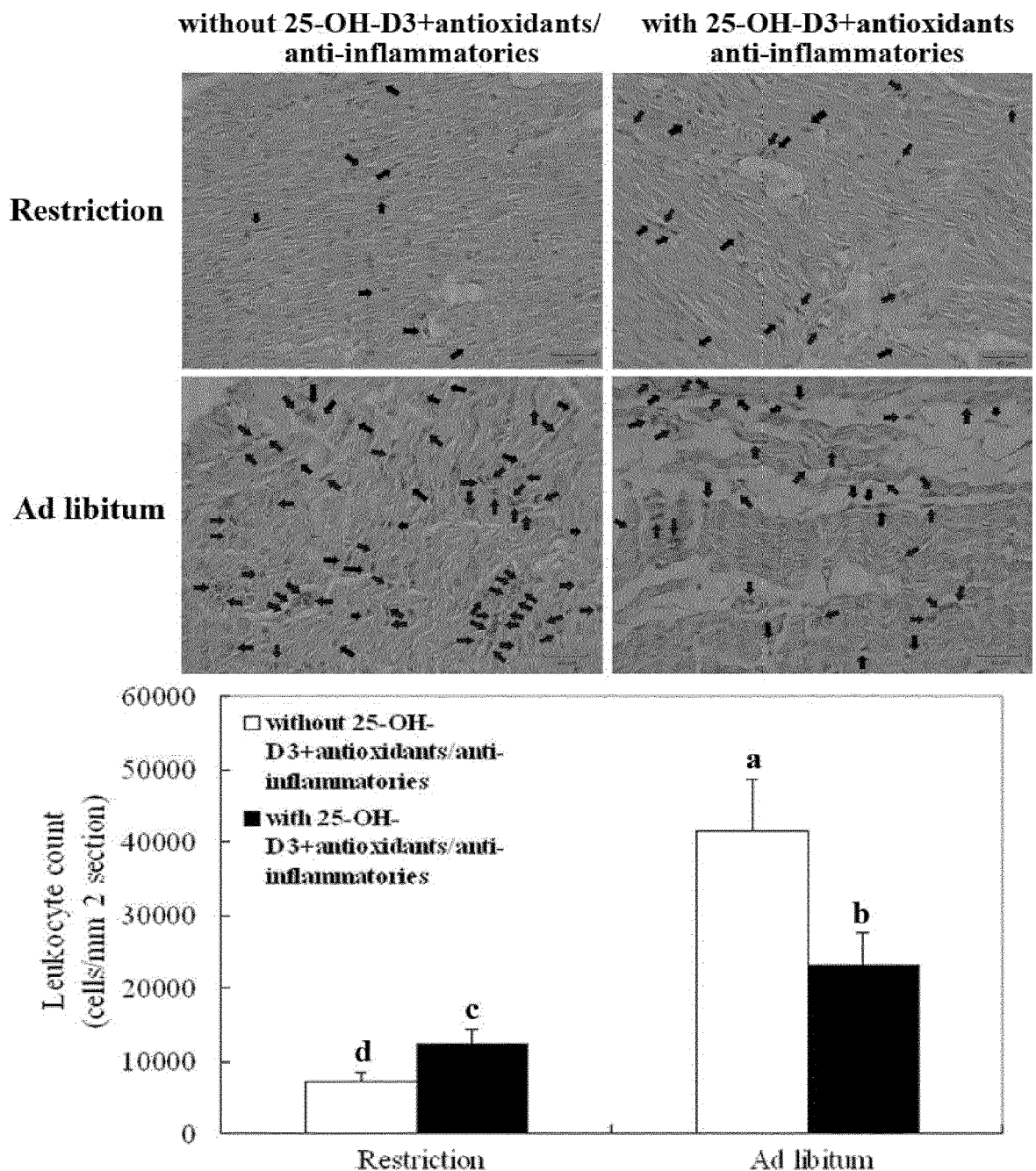
FIGS. 16 and 17 are photos showing the effect of dietary supplementation of 25-OH-D3+antioxidants/anti-inflammatories on cardiac cell apoptosis of broiler hens with restricted or ad libitum feed intake. (at age of 35 weeks)
Figure 17:
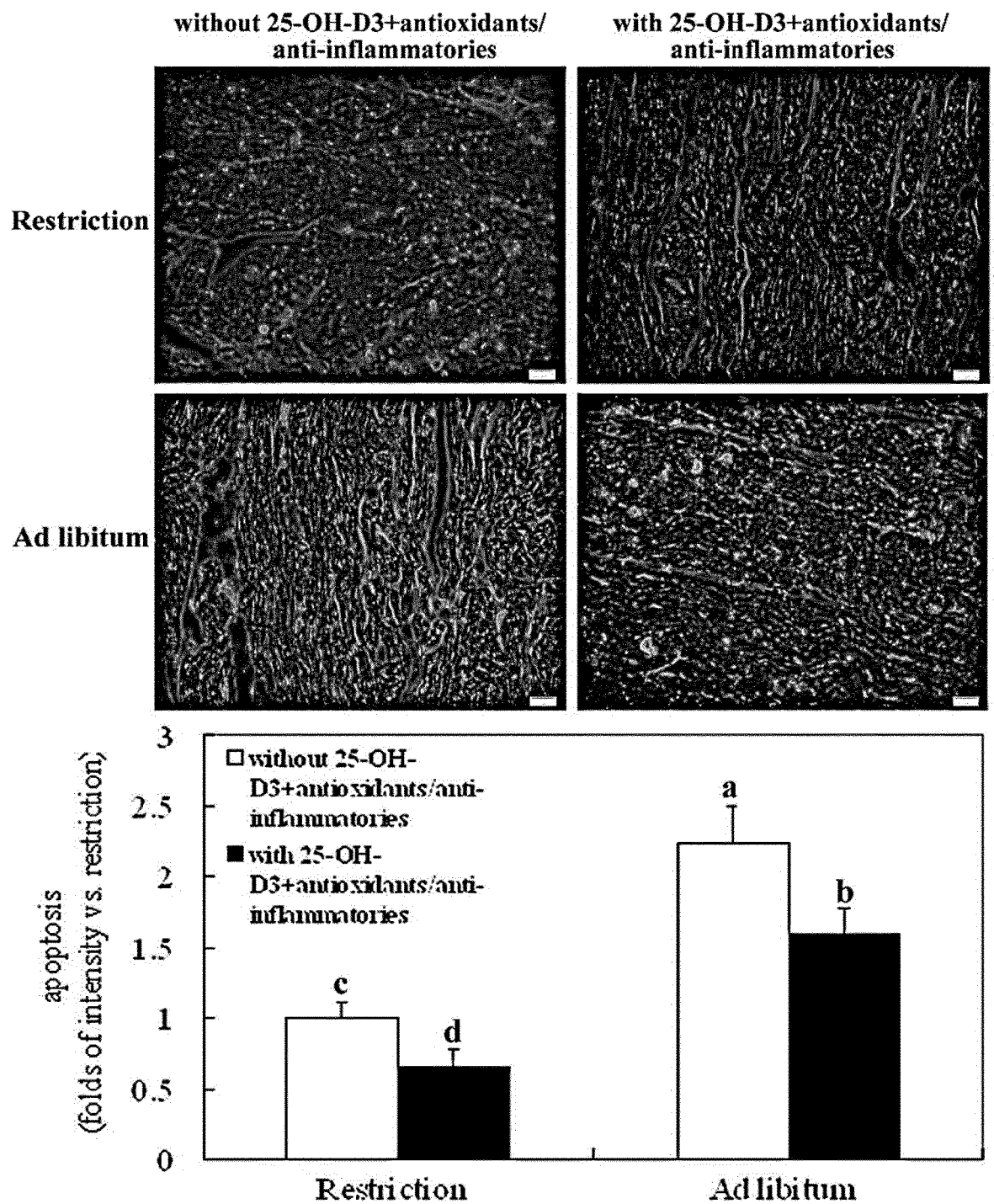

FIG. 16 shows the effect of dietary supplementation of 25-OH-D3+antioxidants/anti-inflammatories on cardiac cell apoptosis of broiler hens with restricted or ad libitum feed intake. (at age of 35 weeks). Results were expressed with

TABLE 19

Effect of dietary supplementation of 25-OH-D3 + antioxidants/anti-inflammatories on electrocardiogram (ECG) pattern and arrhythmia of broiler hens with restricted or ad libitum feed intake. See FIGS. 12 and 13 for examples of the EGC patterns.

|  | Restriction (n = 8) | Restriction + 25-OH-D3 + antioxidant/anti-inflammatories (n = 8) | Ad libitum (n = 8) | Ad libitum + 25-OH-D3 + antioxidant/anti-inflammatories (n = 8) |
|---|---|---|---|---|
| ECG pattern A at age of 35 wks | 4/8 | 4/8 | 1/8 | 3/8 |
| ECG pattern B or C at age of 35 wks | 2/8 | 3/8 | 2/8 | 3/8 |
| ECG pattern D, E, F, or G at age of 35 weeks | 2/8 | 1/8 | 5/8 | 2/8 |
| ECG pattern A at age of 50 wks | 3/8 | 4/8 | 0/8 | 2/8 |
| ECG pattern B or C at age of 50 wks | 3/8 | 2/8 | 1/8 | 3/8 |
| ECG pattern D, E, F, or G at age of 50 weeks | 2/8 | 2/8 | 7/8 | 3/8 |
| Arrhythmic ECG pattern at age of 35 wks | 0/8 | 0/8 | 2/8 | 1/8 |
| Arrhythmic ECG pattern at age of 50 wks | 1/8 | 1/8 | 4/8 | 2/8 |

Figure 12:
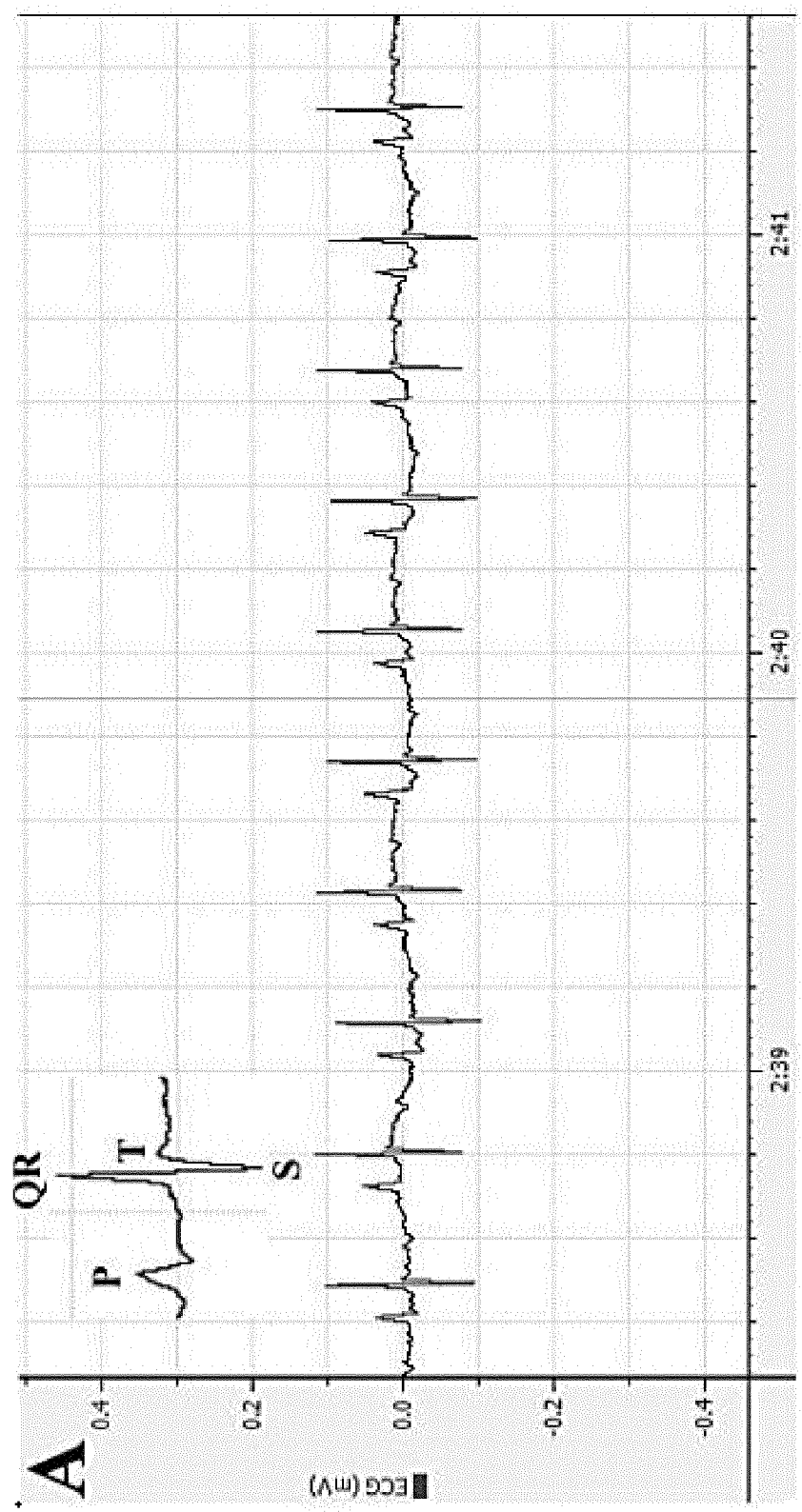
FIG. 12 is a series of electrocardiograms (EGCs) demonstrating the effect of dietary supplementation of 25-OH-D3+antioxidants/anti-inflammatories on EGC of broiler hens with restricted or ad libitum feed intake. The arrows point to irregularities in the patterns.
Figure 13:
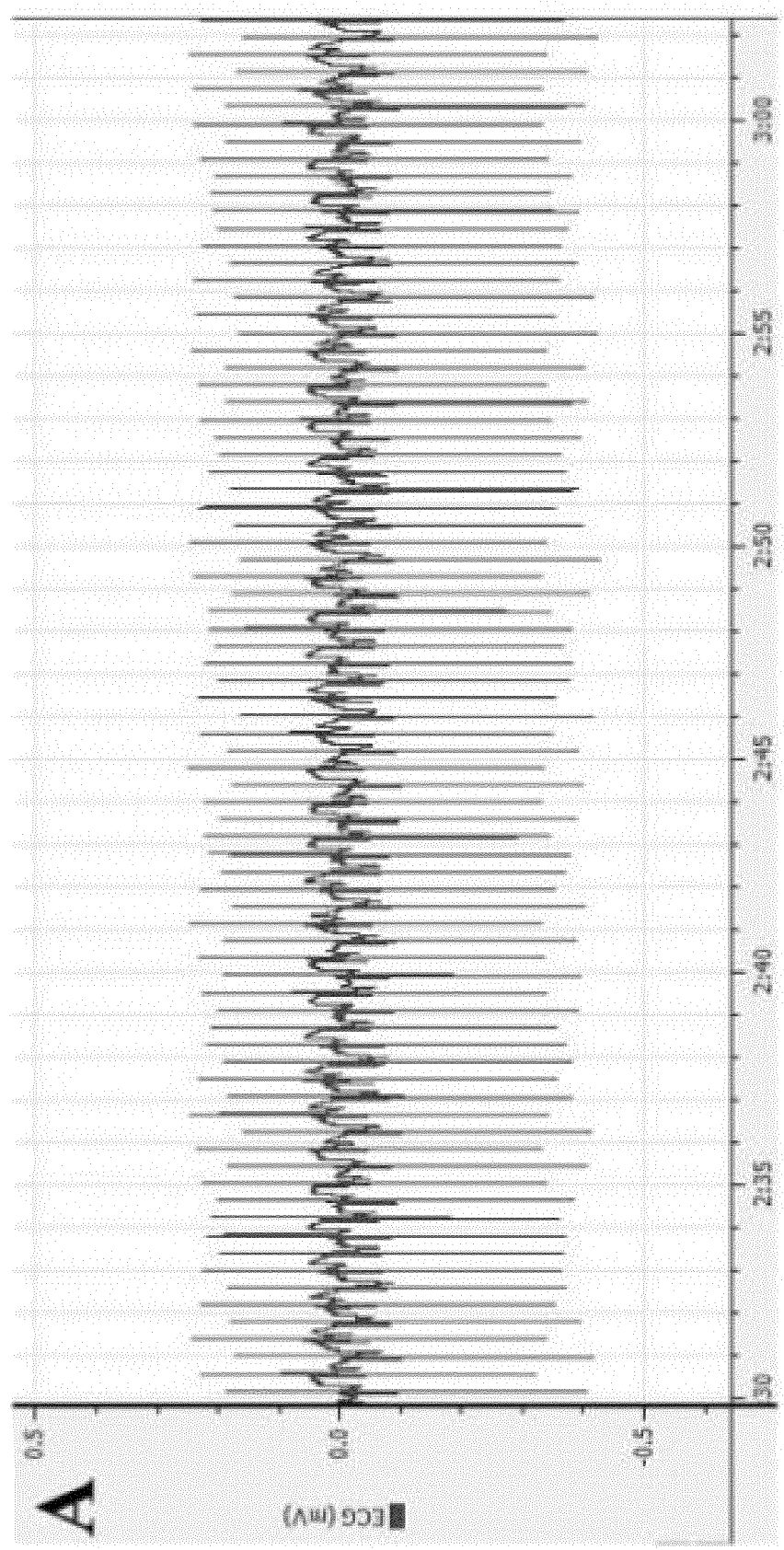
FIG. 13 is a series of EGSs showing the effect of dietary supplementation of 25-OH-D3+antioxidants/anti-inflammatories on arrhythmic ECG pattern of broiler hens with restricted or ad libitum feed intake.

Conclusions and annotations from Table 19 and FIGS. 12 and 13:

mean±SEM (n=3). Means with different letters over the bars are significantly different (P<0.05)

Conclusions and annotations from FIG. 16:
1. 25-OH-D3+antioxidants/anti-inflammatories ameliorated cardiac cell apoptosis in hens with restricted or ad libitum feed intake.

CONCLUSIONS

Supplemental 25-OH D3 and antioxidants/anti-inflammatories ameliorated deleterious effects associated with overfeeding of broiler breeder females by:
- lowering mortality rate and improving ovary function and therefore reproductive performance of overfed broiler breeder hens.
- improving endocrine (insulin) signaling
- reducing lipotoxic development and systemic inflammation
- activating cardio-protective mechanisms against fuel-overload induced cardiac pathogenesis.

The invention claimed is:
1. A method of ameliorating a symptom of polycystic ovary syndrome in a vitamin replete person at risk of developing the syndrome, comprising:
   administering to a vitamin replete person who has polycystic ovary syndrome or who is at risk of developing polycystic ovary syndrome an effective amount of a daily dosage combination comprising:
   1 µg to 50 µg 25-hydroxyvitamin D3, 1-1000 mg/day Vitamin C, 5-750 mg Vitamin E, and one or more carotenoids selected from the group consisting of: 1-150 mg astaxanthin, 1-100 mg β-cryptoxanthin, 1-100 mg beta-carotene, 1-100 mg lutein, 1-60 mg zeaxanthin and not more than 30 mg canthaxanthin, wherein the daily dosage combination does not include lycopene.

* * * * *